United States Patent
Horiuchi et al.

(10) Patent No.: US 10,754,425 B2
(45) Date of Patent: Aug. 25, 2020

(54) INFORMATION PROCESSING APPARATUS, INFORMATION PROCESSING METHOD, AND NON-TRANSITORY COMPUTER READABLE RECORDING MEDIUM

(71) Applicant: OLYMPUS CORPORATION, Tokyo (JP)

(72) Inventors: Kazuhito Horiuchi, Hachioji (JP);
Nobuyuki Watanabe, Yokohama (JP);
Yoshioki Kaneko, Hachioji (JP);
Hidetoshi Nishimura, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/412,513

(22) Filed: May 15, 2019

(65) Prior Publication Data
US 2019/0354177 A1 Nov. 21, 2019

(30) Foreign Application Priority Data

May 17, 2018 (JP) .................................. 2018-095519
May 8, 2019 (JP) .................................. 2019-088251

(51) Int. Cl.
*G06F 3/01* (2006.01)
*G10L 15/26* (2006.01)
*G10L 15/22* (2006.01)

(52) U.S. Cl.
CPC .............. *G06F 3/013* (2013.01); *G06F 3/012* (2013.01); *G10L 15/22* (2013.01); *G10L 15/26* (2013.01)

(58) Field of Classification Search
CPC .... G06F 2203/011; G06F 3/012; G06F 3/013; G06F 3/16; G10L 15/22; G10L 15/26
USPC .................................................. 345/672, 156
See application file for complete search history.

(56) References Cited

U.S. PATENT DOCUMENTS

| | | | | |
|---|---|---|---|---|
| 7,246,062 | B2* | 7/2007 | Knott | G10L 15/22 704/246 |
| 7,933,508 | B2* | 4/2011 | Konicek | G03B 17/02 396/51 |
| 8,311,835 | B2* | 11/2012 | Lecoeuche | H04M 1/72561 704/270 |
| 8,467,672 | B2* | 6/2013 | Konicek | H04N 5/232 396/56 |
| 8,612,223 | B2* | 12/2013 | Minamino | G10L 15/183 704/231 |
| 10,176,365 | B1* | 1/2019 | Ramanarayanan | G06K 9/00335 |
| 10,475,448 | B2* | 11/2019 | Furumoto | G10L 15/22 |

(Continued)

FOREIGN PATENT DOCUMENTS

| JP | 4282343 B2 | 6/2009 |
|---|---|---|
| JP | 2016-181245 A | 10/2016 |

*Primary Examiner* — Tony O Davis
(74) *Attorney, Agent, or Firm* — Scully, Scott, Murphy & Presser, P.C.

(57) ABSTRACT

An information processing apparatus is disclosed which includes a hardware processor configured to, analyze an attention degree of a gaze of a user, on the basis of gaze data in which the gaze of the user is detected, the gaze data being input externally, and assign an important degree according to the attention degree that is analyzed with respect to speech data of the user, the speech data being input externally, and is associated with a time axis that is a same as that of the gaze data to be recorded in a memory.

5 Claims, 23 Drawing Sheets

(56) References Cited

U.S. PATENT DOCUMENTS

| | | | |
|---|---|---|---|
| 2009/0112617 A1* | 4/2009 | Jung | G06F 19/3418 705/2 |
| 2009/0112621 A1* | 4/2009 | Jung | G06F 19/328 705/2 |
| 2009/0118593 A1* | 5/2009 | Jung | G06Q 50/22 600/300 |
| 2009/0119154 A1* | 5/2009 | Jung | G06Q 30/02 705/7.33 |
| 2009/0132275 A1* | 5/2009 | Jung | A61B 5/16 705/2 |
| 2009/0156907 A1* | 6/2009 | Jung | A61B 5/0476 600/300 |
| 2009/0156955 A1* | 6/2009 | Jung | A61B 5/0476 600/544 |
| 2009/0157481 A1* | 6/2009 | Jung | A61B 5/0476 709/205 |
| 2009/0157482 A1* | 6/2009 | Jung | A61B 5/04842 705/7.33 |
| 2009/0157625 A1* | 6/2009 | Jung | G06N 20/00 |
| 2009/0157660 A1* | 6/2009 | Jung | G06Q 30/00 |
| 2009/0157751 A1* | 6/2009 | Jung | A61B 5/14553 |
| 2009/0157813 A1* | 6/2009 | Jung | G06N 20/00 709/204 |
| 2009/0163777 A1* | 6/2009 | Jung | A61B 5/04842 600/301 |
| 2009/0164131 A1* | 6/2009 | Jung | A61B 5/16 702/19 |
| 2009/0164132 A1* | 6/2009 | Jung | G16B 45/00 702/19 |
| 2009/0164302 A1* | 6/2009 | Jung | G06Q 30/02 705/7.33 |
| 2009/0164401 A1* | 6/2009 | Jung | G06Q 30/02 706/45 |
| 2009/0164403 A1* | 6/2009 | Jung | G06N 5/02 706/46 |
| 2009/0164458 A1* | 6/2009 | Jung | G06Q 30/02 |
| 2009/0164503 A1* | 6/2009 | Jung | G06F 16/436 |
| 2009/0164549 A1* | 6/2009 | Jung | G06Q 30/02 709/201 |
| 2009/0171164 A1* | 7/2009 | Jung | A61B 5/04842 600/300 |
| 2009/0172540 A1* | 7/2009 | Jung | A61B 5/744 715/706 |
| 2009/0267758 A1* | 10/2009 | Hyde | A61B 5/0002 340/539.12 |
| 2009/0271011 A1* | 10/2009 | Hyde | G06F 19/326 700/28 |
| 2009/0271120 A1* | 10/2009 | Hyde | G06F 19/326 702/19 |
| 2009/0271347 A1* | 10/2009 | Hyde | G06F 19/326 706/46 |
| 2009/0312595 A1* | 12/2009 | Leuthardt | G06F 19/3481 600/27 |
| 2009/0312668 A1* | 12/2009 | Leuthardt | G06F 19/3481 600/558 |
| 2009/0318773 A1* | 12/2009 | Jung | A61B 5/04009 600/300 |
| 2009/0326937 A1* | 12/2009 | Chitsaz | G10L 15/24 704/235 |
| 2010/0004762 A1* | 1/2010 | Leuthardt | G06F 19/3481 700/28 |
| 2010/0015583 A1* | 1/2010 | Leuthardt | G06F 19/3481 434/236 |
| 2010/0017001 A1* | 1/2010 | Leuthardt | G06F 19/3481 700/94 |
| 2010/0022820 A1* | 1/2010 | Leuthardt | G06F 19/3481 600/27 |
| 2010/0041958 A1* | 2/2010 | Leuthardt | G06F 19/3481 600/300 |
| 2010/0042578 A1* | 2/2010 | Leuthardt | G06F 19/3481 706/59 |
| 2010/0063368 A1* | 3/2010 | Leuthardt | G06F 19/3481 600/301 |
| 2010/0069724 A1* | 3/2010 | Leuthardt | G06F 19/3481 600/301 |
| 2010/0076249 A1* | 3/2010 | Leuthardt | G06F 19/3456 600/27 |
| 2010/0081860 A1* | 4/2010 | Leuthardt | G06F 19/3481 600/27 |
| 2010/0081861 A1* | 4/2010 | Leuthardt | G06F 19/3481 600/27 |
| 2010/0100036 A1* | 4/2010 | Leuthardt | G06F 19/3481 604/65 |
| 2010/0118200 A1* | 5/2010 | Gelman | G06F 3/041 348/578 |
| 2010/0125561 A1* | 5/2010 | Leuthardt | G06F 19/3481 707/706 |
| 2010/0130811 A1* | 5/2010 | Leuthardt | G06F 19/3481 600/27 |
| 2010/0163027 A1* | 7/2010 | Hyde | A61M 15/00 128/203.12 |
| 2010/0163035 A1* | 7/2010 | Hyde | A61M 15/02 128/203.14 |
| 2010/0168525 A1* | 7/2010 | Hyde | A61B 5/14532 600/300 |
| 2010/0168602 A1* | 7/2010 | Hyde | A61M 11/00 600/544 |
| 2010/0241449 A1* | 9/2010 | Firminger | G06F 19/3418 705/2 |
| 2010/0268057 A1* | 10/2010 | Firminger | G06F 19/328 600/407 |
| 2010/0268108 A1* | 10/2010 | Firminger | G06F 19/328 600/544 |
| 2010/0274577 A1* | 10/2010 | Firminger | G06F 19/328 705/2 |
| 2010/0274578 A1* | 10/2010 | Firminger | G06F 19/328 705/2 |
| 2010/0280332 A1* | 11/2010 | Hyde | G06F 19/3481 600/301 |
| 2010/0293002 A1* | 11/2010 | Firminger | G06F 19/3418 705/2 |
| 2010/0305962 A1* | 12/2010 | Firminger | G06F 19/3481 705/2 |
| 2010/0305963 A1* | 12/2010 | Firminger | G06F 19/3481 705/2 |
| 2010/0312579 A1* | 12/2010 | Firminger | G06F 19/3481 705/3 |
| 2011/0035231 A1* | 2/2011 | Firminger | G06F 19/3418 705/2 |
| 2012/0164613 A1* | 6/2012 | Jung | G06Q 30/02 434/236 |
| 2013/0316322 A1* | 11/2013 | Roschelle | G09B 7/00 434/350 |
| 2013/0316323 A1* | 11/2013 | Roschelle | G09B 7/00 434/350 |
| 2014/0168277 A1* | 6/2014 | Ashley | G06F 3/1446 345/672 |
| 2015/0127340 A1* | 5/2015 | Epshteyn | G10L 15/26 704/235 |
| 2016/0080684 A1* | 3/2016 | Farrell | H04N 9/8211 386/227 |
| 2018/0133900 A1* | 5/2018 | Breazeal | B25J 11/0015 |
| 2018/0268737 A1* | 9/2018 | Garnavi | G09B 7/06 |

* cited by examiner

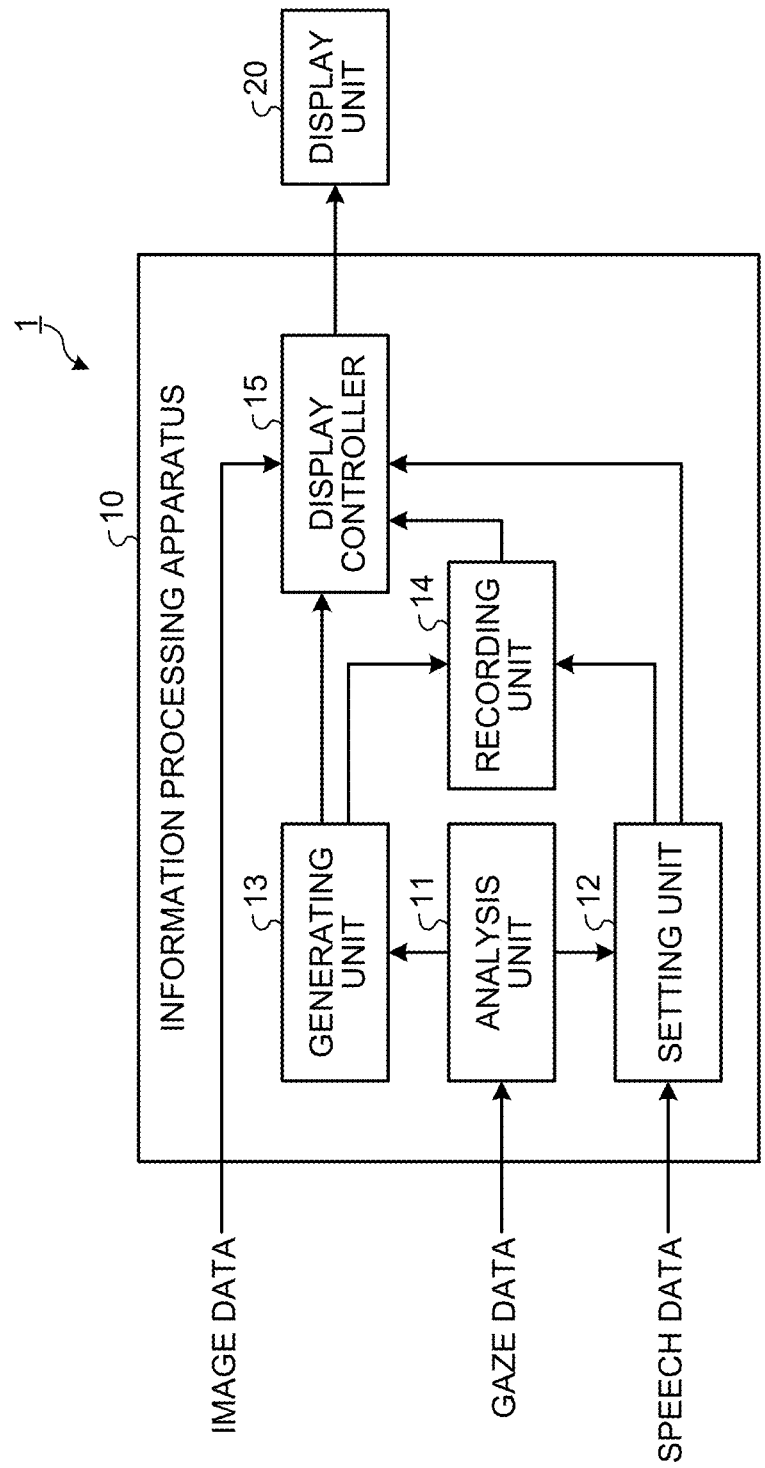

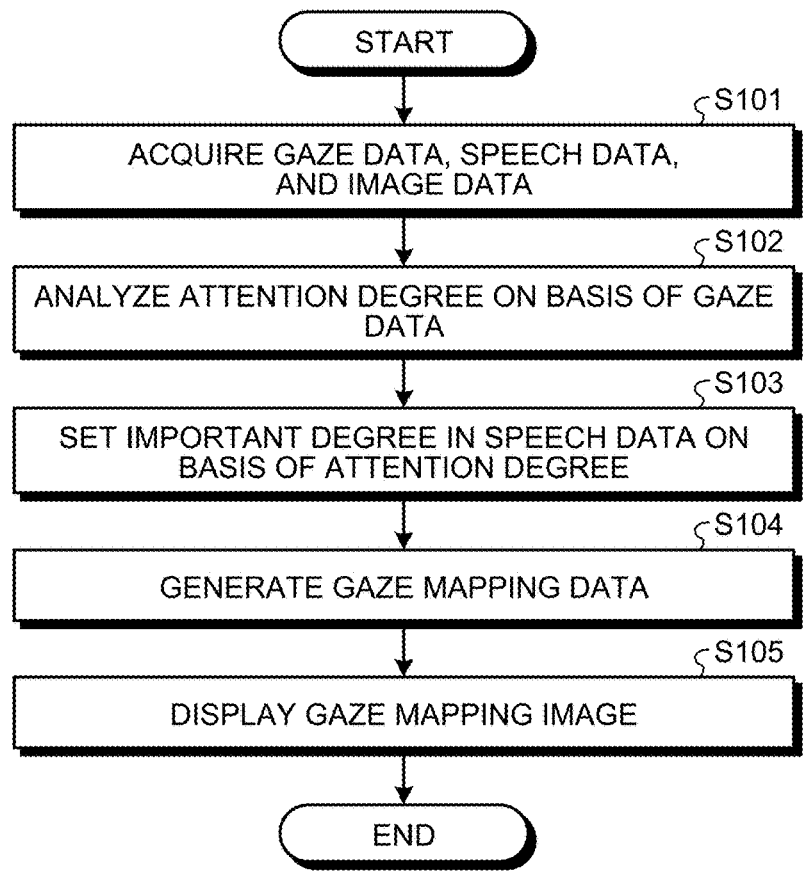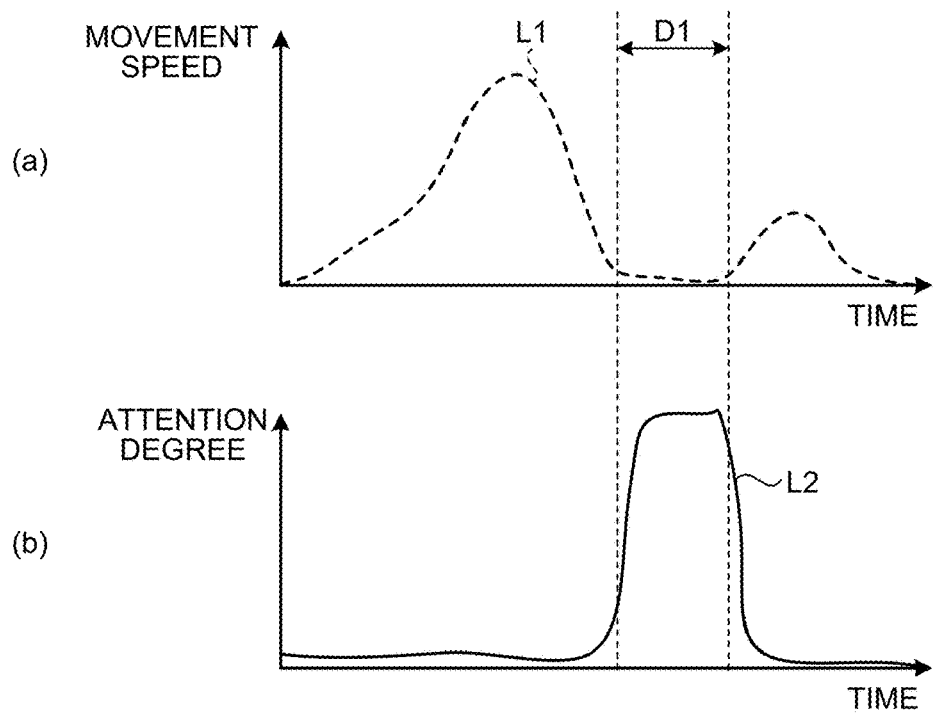

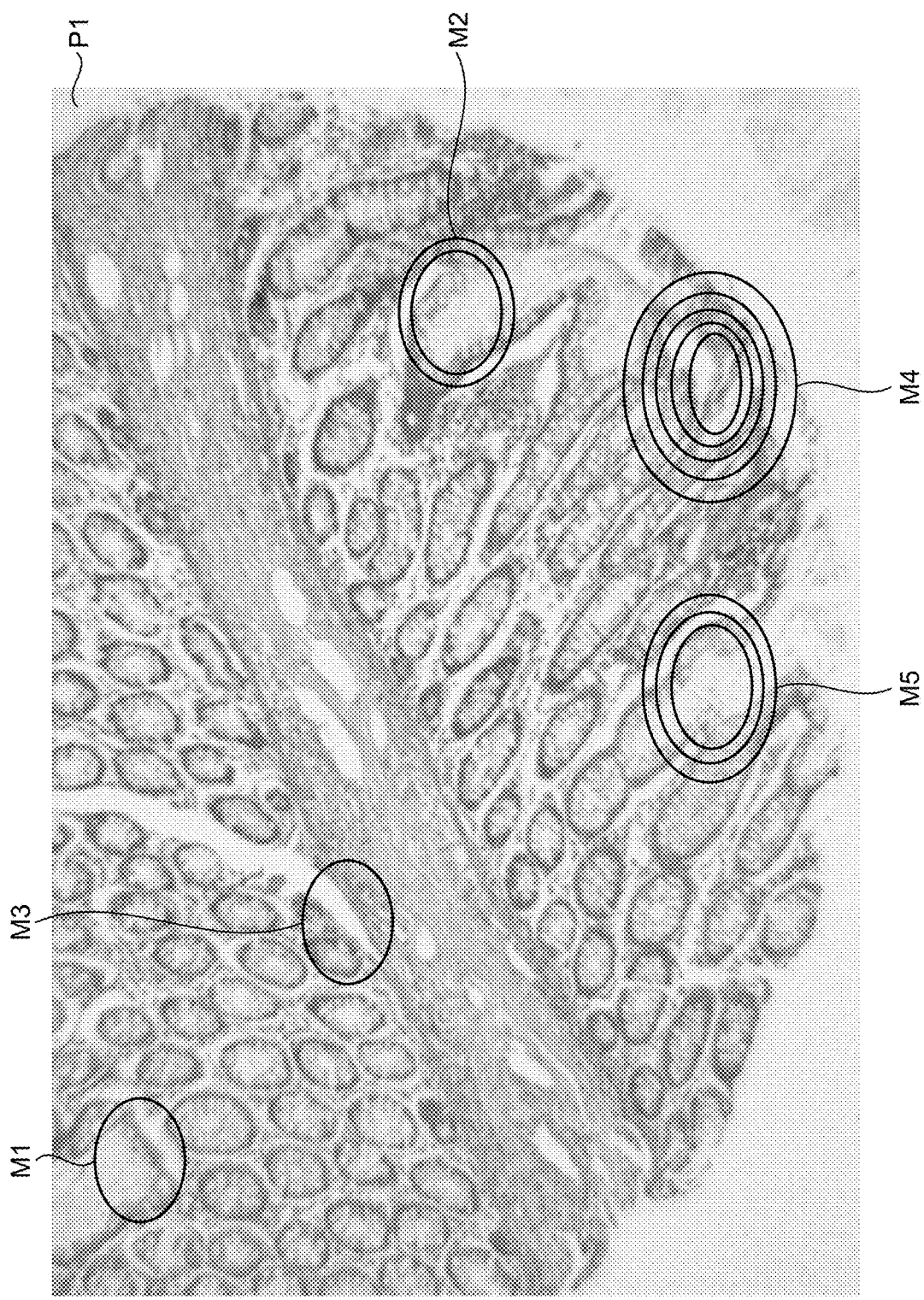

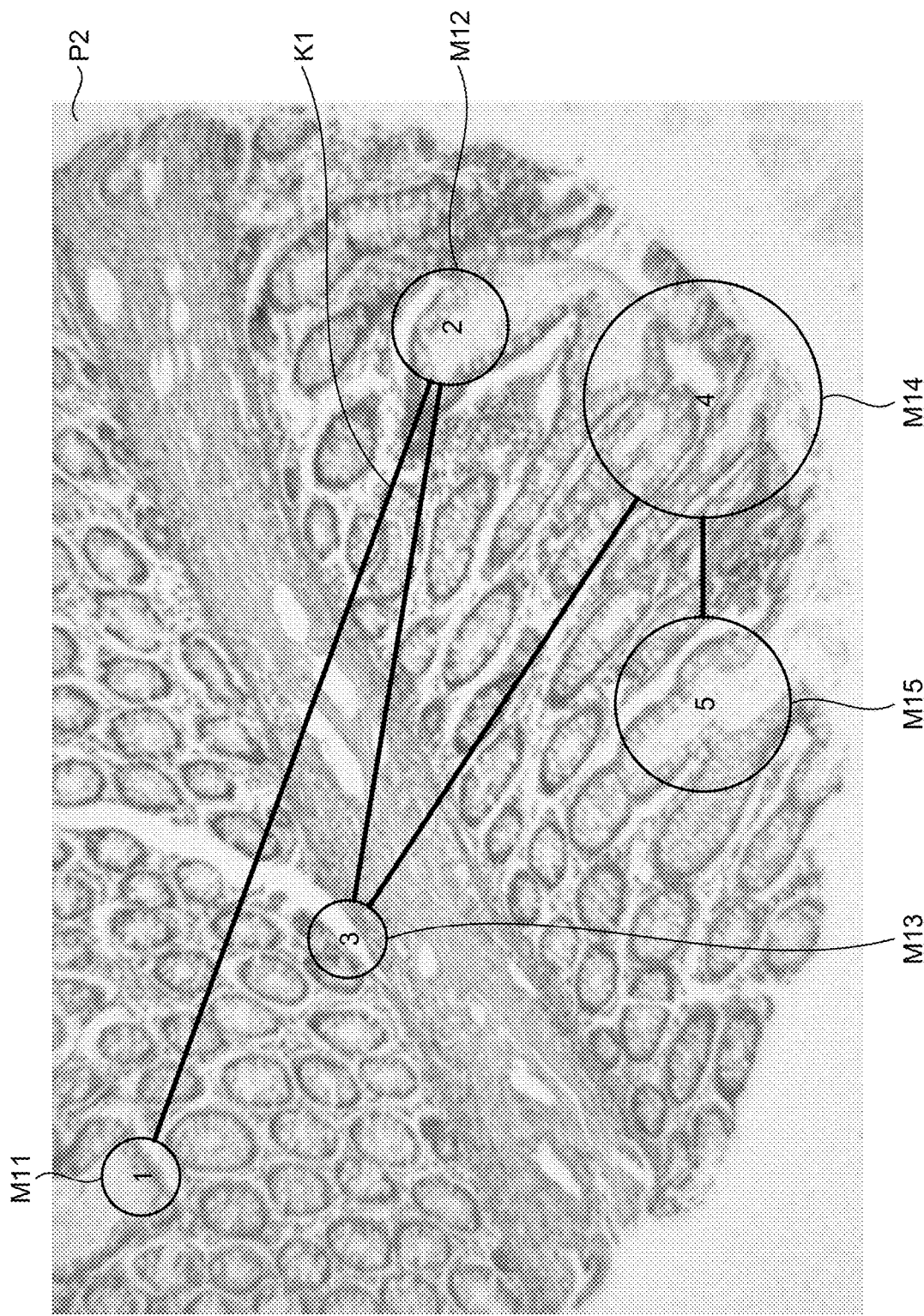

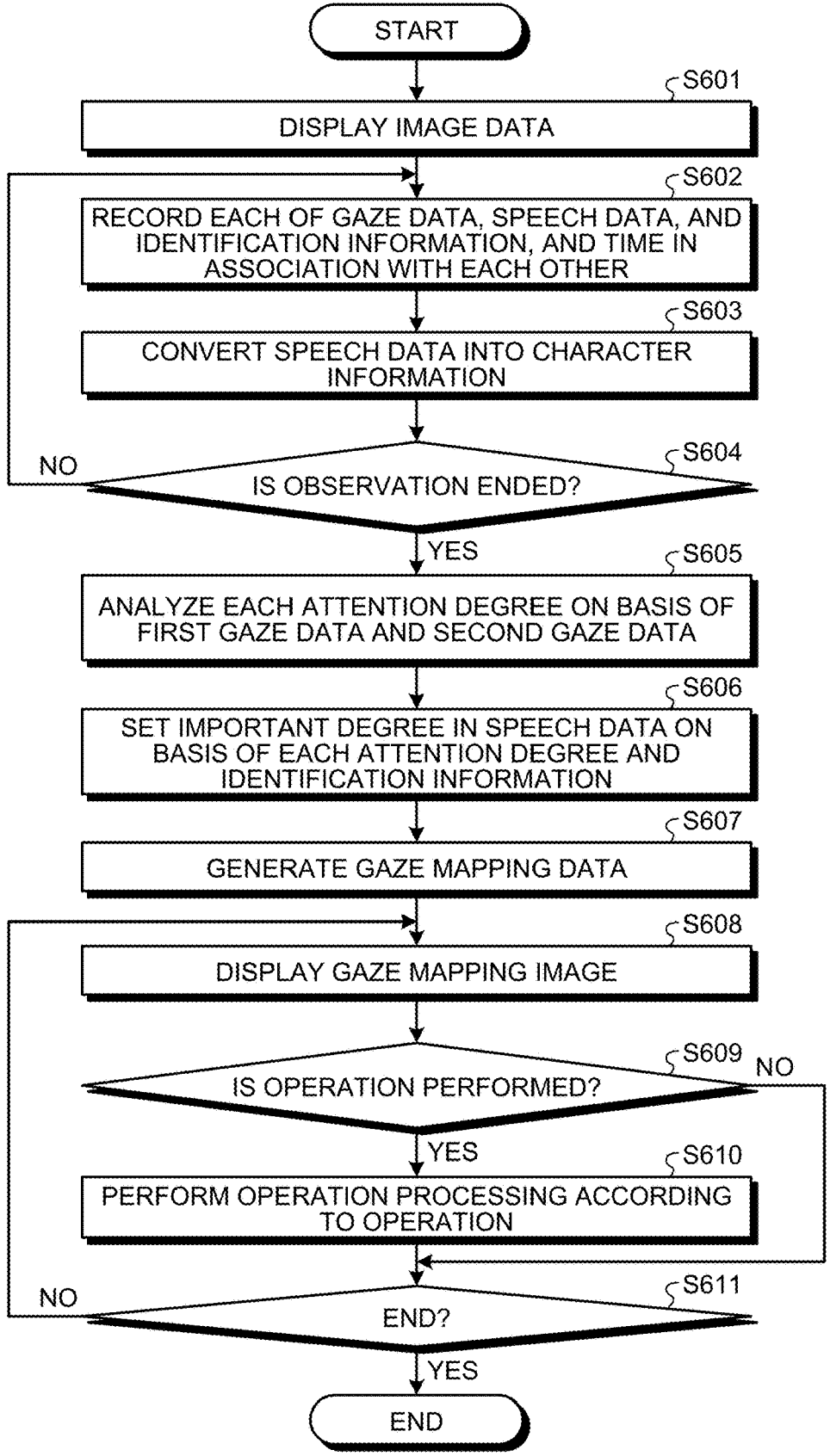

INFORMATION PROCESSING APPARATUS, INFORMATION PROCESSING METHOD, AND NON-TRANSITORY COMPUTER READABLE RECORDING MEDIUM

CROSS-REFERENCE TO RELATED APPLICATIONS

This application is based upon and claims the benefit of priority from Japanese Patent Application No. 2018-095519, filed on May 17, 2018 and Japanese Patent Application No. 2019-088251, filed on May 8, 2019, the entire contents of which are incorporated herein by reference.

BACKGROUND

The present disclosure relates to an information processing apparatus that processes speech data and gaze data, an information processing method, and a non-transitory computer readable recording medium.

Recently, in an information processing apparatus that processes information such as image data, a technology is known in which in a period tracing back to a predetermined time from a time when a speech of a user is detected, a display area of an image at which a gaze of the user stays for the longest period is detected as attention information with respect to a plurality of display areas on an image that is displayed on a display unit, and the attention information and the speech are recorded by being associated with each other (refer to Japanese Patent Publication No. 4282343).

In addition, in an attention annotation system, a technology is known in which an annotation anchor is displayed close to an attention point at which a user gazes, detected by a gazing tracking device, with respect to an image that is displayed on a display device of a computing device, and information is input into the annotation anchor by a speech (refer to Japanese Laid-open Patent Application Publication 2016-181245).

SUMMARY

According to a first aspect of the present disclosure, an information processing apparatus is provided which includes a hardware processor configured to, analyze an attention degree of a gaze of a user, on the basis of gaze data in which the gaze of the user is detected, the gaze data being input externally, and assign an important degree according to the attention degree that is analyzed with respect to speech data of the user, the speech data being input externally, and is associated with a time axis that is a same as that of the gaze data to be recorded in a memory.

According to a second aspect of the present disclosure, An information processing method to be executed by an information processing apparatus, the method including analyzing an attention degree of a gaze of a user, on the basis of gaze data in which the gaze of the user is detected, the gaze data being input externally; and assigning an important degree according to the attention degree that is analyzed in the analysis step with respect to speech data of the user, the speech data being input externally, and is associated with a time axis that is a same as that of the gaze data to be recorded in a memory.

According to a third aspect of the present disclosure, a non-transitory computer readable recording medium is provided which records a program of allowing an information processing apparatus to execute: analyzing an attention degree of a gaze of a user, on the basis of gaze data in which the gaze of the user is detected, the gaze data being input externally; and assigning an important degree according to the attention degree that is analyzed in the analysis step with respect to speech data of the user, the speech data being input externally, and is associated with a time axis that is a same as that of the gaze data to be recorded in a memory.

BRIEF DESCRIPTION OF THE DRAWINGS

FIG. 1 is a block diagram illustrating a functional configuration of an information processing system according to a first embodiment;

FIG. 2 is a flowchart illustrating processing that is executed by an information processing apparatus according to the first embodiment;

FIG. 3 is a diagram schematically illustrating an analysis method of an attention degree of a gaze of an analysis unit according to the first embodiment;

FIG. 5 is a diagram schematically illustrating an example of an image that is displayed on a display unit according to the first embodiment;

FIG. 6 is a diagram schematically illustrating another example of the image that is displayed on the display unit according to the first embodiment;

FIG. 24 is a flowchart illustrating an outline of processing that is executed by the information processing system according to the fifth embodiment.

DETAILED DESCRIPTION OF THE PREFERRED EMBODIMENTS

Figure 4A:
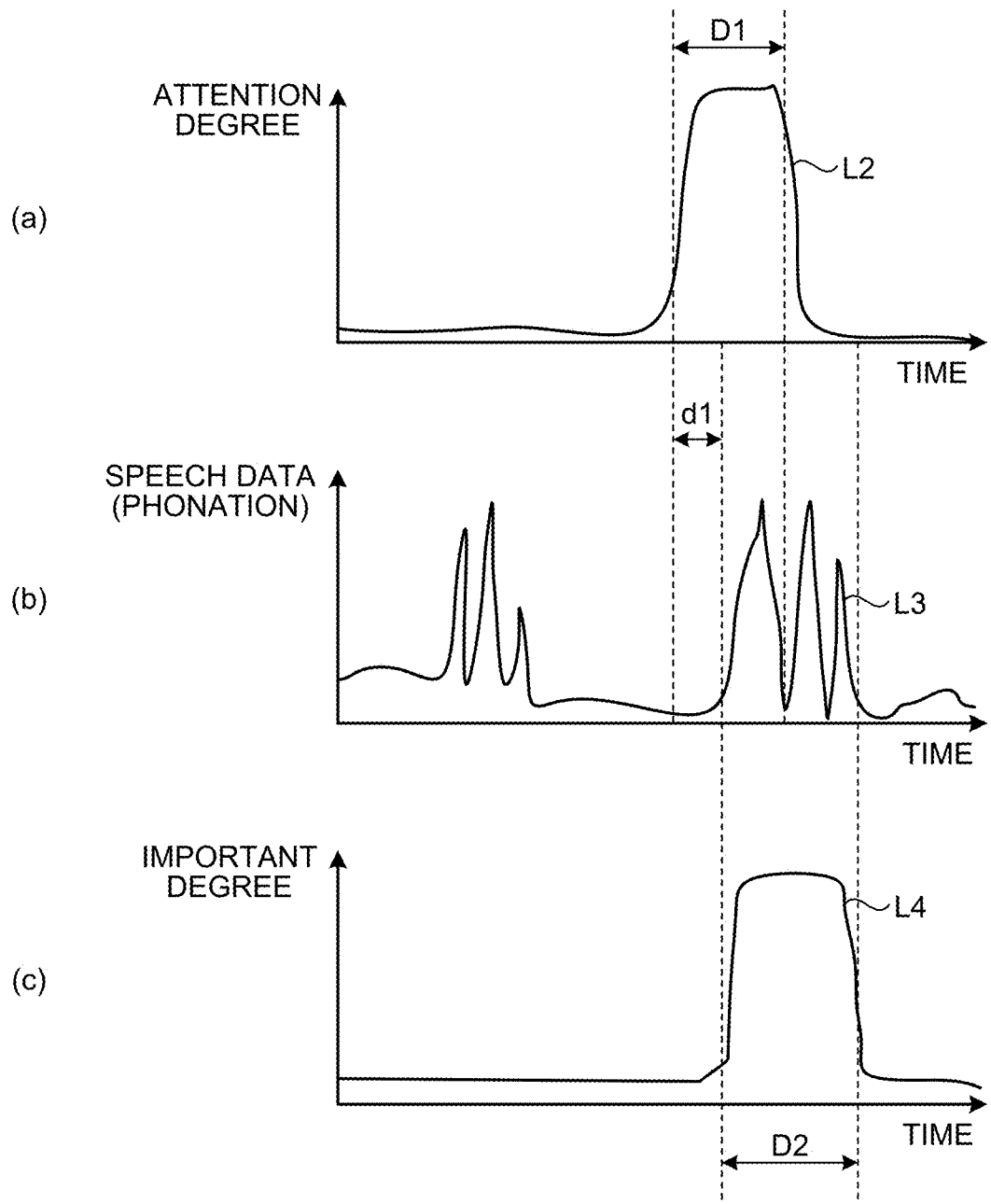
FIG. 4A is a diagram schematically illustrating a setting method of assigning an important degree to speech data of a setting unit according to the first embodiment.

Hereinafter, modes for carrying out the present disclosure will be described in detail along with the drawings. The present disclosure is not limited by the following embodiments. In addition, each of the drawings referred to by the following description merely schematically illustrates a shape, a size, and a position relationship to the extent that the contents of the present disclosure can be understood. That is, the present disclosure is not limited to the shape, the size, and the position relationship exemplified in each of the drawings.

First Embodiment

Configuration of Information Processing System

FIG. 1 is a block diagram illustrating a functional configuration of an information processing system according to a first embodiment. An information processing system 1 illustrated in FIG. 1 includes an information processing apparatus 10 performing various pieces of processing with respect to gaze data, speech data, and image data that is input externally, and a display unit 20 displaying various kinds of data that are output from the information processing apparatus 10. Furthermore, the information processing apparatus 10 and the display unit 20 are bidirectionally connected wirelessly or by wire.

Configuration of Information Processing Apparatus

First, the configuration of the information processing apparatus 10 will be described.

The information processing apparatus 10 illustrated in FIG. 1, for example, is realized by using a program that is installed in a server, a personal computer, or the like, and various kinds of data are input through a network, or various kinds of data that are acquired by an external device are input into the information processing apparatus 10. As illustrated in FIG. 1, the information processing apparatus 10 includes an analysis unit 11, a setting unit 12, a generating unit 13, a recording unit 14, and a display controller 15.

The analysis unit 11 analyzes an attention degree of a gaze of a user, on the basis of gaze data of a predetermined time in which the gaze of the user is detected, the gaze data being input externally. Here, the gaze data is based on a cornea reflection method. Specifically, the gaze data is data that is generated by capturing a pupil point and a reflex point on the cornea with an optical sensor that is a gaze detection unit when the cornea of the user cornea is irradiated with a near infrared ray from an LED light source or the like that is provided in the unillustrated gaze detection unit (eye tracking). Additionally, regarding the gaze data, the gaze of the user is calculated from the pattern of the pupil point and the reflex point of the user based on an analysis result analyzed by performing image processing or the like with respect to the data that is generated by the optical sensor capturing the pupil point and the reflex point on the cornea.

In addition, even though it is not illustrated, when a device including the gaze detection unit measures the gaze data, the corresponding image data is presented to the user, and then, the gaze data is measured. In this case, in a case where an image that is displayed to the user is fixed, that is, when absolute coordinates are not changed along with a time of a display area, the device including the gaze detection unit (not illustrated) may apply a relatively position relationship between a measurement area and the absolute coordinates of the image to the gaze, as a fixed value. Here, the absolute coordinates indicate coordinates described on the basis of one predetermined point of the image.

In a case where a utilization form is an endoscope system or an optical microscope, in the analysis unit 11, a field of view that is presented in order to detect the gaze is a field of view of the image data, and thus, a relative position relationship of an observation field of view with respect to the absolute coordinates of the image is not changed. In addition, in a case where the utilization form is the endoscope system or the optical microscope, in the analysis unit 11, gaze detection data, an image recorded or presented along with the detection of the gaze are used in order to generate mapping data of the field of view at the time of being recorded as a moving image.

On the other hand, in a case where the utilization form is whole slide imaging (WSI), the user observes a part of a slide sample of a microscope, as the field of view, and the observation field of view is changed along with a time. In this case, in the analysis unit 11, it is considered that a portion of the entire image data is presented as the field of view, that is, time information of switching the absolute coordinates of the display area with respect to the entire image data is also recorded by being synchronized with the information of the gaze and the speech.

The analysis unit 11 detects any one of a moving speed of the gaze, a moving distance of the gaze within a predetermined time, and a residence time of the gaze within in a prescribed area, on the basis of the gaze data, which is input externally, within a predetermined time in which the gaze of the user is detected, and thus, analyzes the attention degree of the gaze (an attention point). Furthermore, the gaze detection unit (not illustrated) may detect the gaze by being provided in a predetermined location, and by capturing the user, or may detect the gaze by being provided in the user wearing, and by capturing the user. In addition, the gaze data may be generated by known pattern matching.

The analysis unit 11, for example, is configured by using a central processing unit (CPU), a field programmable gate array (FPGA), a graphics processing unit (GPU), and the like.

The setting unit 12 assigns an important degree according to the attention degree analyzed by the analysis unit 11 at a predetermined time interval with respect to the speech data of the user, the speech data being input externally, and is associated with a time axis identical to that of the gaze data to be recorded in the recording unit 14. Specifically, the setting unit 12 assigns the important degree (for example, a numerical value) according to the attention degree that is analyzed by the analysis unit 11 at the same timing of the frame to each frame of the speech data to be recorded in the recording unit 14. In addition, the speech data of the user, the speech data being input externally is generated at the same timing as that of the gaze data by a speech input unit such as microphone (not illustrated). The setting unit 12 is configured by using a CPU, an FPGA, a GPU, and the like.

The generating unit 13 generates gaze mapping data in which the attention degree that is analyzed by the analysis unit 11 is associated with an image corresponding to the image data that is input externally, and outputs the generated gaze mapping data to the recording unit 14 and the display controller 15. Specifically, the generating unit 13 generates the gaze mapping data in which the attention degree that is analyzed by the analysis unit 11 is associated with the coordinate information on the image at each predetermined area on the image corresponding to the image data that is input externally. Further, the generating unit 13 generates the gaze mapping data by associating the locus of the gaze of the user that is analyzed by the analysis unit 11 with the image corresponding to the image data that is input externally, in addition to the attention degree. The generating unit 13 is configured by using a CPU, an FPGA, a GPU, and the like. Then, in the case of the WSI described above, at the time of obtaining the gaze mapping data as the absolute coordinates of the image, the generating unit 13 generates the gaze mapping data by using a relative position relationship between display at the time of measuring the gaze and the absolute coordinates of the image. In addition, as described above, in a case where the observation field of view is changed every moment, the generating unit 13 inputs a temporal change in absolute coordinates of Display Area=Field of view (for example, in which portion of the original image data the upper left side of the display image is positioned on the absolute coordinates), and thus, generates the gaze mapping data.

The recording unit 14 records the speech data that is input from the setting unit 12, the important degree that is assigned at each predetermined time interval, and the attention degree that is analyzed by the analysis unit 11 in association with each other. In addition, the recording unit 14 records the gaze mapping data that is input from the generating unit 13. In addition, the recording unit 14 records various programs that are executed by the information processing apparatus 10, and data in the processing. The recording unit 14 is configured by using a volatile memory, a non-volatile memory, a recording medium, and the like.

The display controller 15 superimposes the gaze mapping data that is generated by the generating unit 13 on the image corresponding to the image data that is input externally, and outputs the gaze mapping data to the external display unit 20 to be displayed. The display controller 15 is configured by using a CPU, an FPGA, a GPU, and the like. Furthermore, the analysis unit 11, the setting unit 12, the gaze mapping, and the display controller 15 described above may be configured such that each function can be exhibited by using any one of a CPU, an FPGA, and a GPU, and may be configured such that each function can be exhibited by a combination of the CPU, the FPGA, and the GPU.

Configuration of Display Unit

Next, the configuration of the display unit 20 will be described.

The display unit 20 displays the image corresponding to the image data that is input from the display controller 15 or gaze mapping information corresponding to gaze mapping data. The display unit 20, for example, is configured by using a display monitor such as an organic electro luminescence (EL) monitor or a liquid crystal monitor.

Processing of Information Processing Apparatus

Next, the processing of the information processing apparatus 10 will be described. FIG. 2 is a flowchart illustrating the processing that is executed by the information processing apparatus 10.

As illustrated in FIG. 2, first, the information processing apparatus 10 acquires the gaze data, the speech data, and the image data that is input externally (Step S101).

Subsequently, the analysis unit 11 analyzes the attention degree of the gaze of the user, on the basis of the gaze data (Step S102). After Step S102, the information processing apparatus 10 proceeds to Step S103 described below.

FIG. 3 is a diagram schematically illustrating an analysis method of the attention degree of the gaze of the analysis unit 11. In (a) of FIG. 3 and (b) of FIG. 3, a horizontal axis represents a time, a vertical axis in (a) of FIG. 3 represents a moving speed, and a vertical axis in (b) of FIG. 3 represents an attention degree. In addition, a curve L1 in (a) of FIG. 3 represents a time change in the moving speed of the gaze; a curve L2 in (b) of FIG. 3 represents a time change in the attention degree.

In general, it is possible to analyze that the attention degree of the user decreases as the moving speed of the gaze increases, and the attention degree of the gaze of the user increases as the moving speed of the gaze decreases. That is, as illustrated by the curve L1 and curve L2 of FIG. 3, the analysis unit 11 analyzes that the attention degree of the gaze of the user decreases as the moving speed of the gaze of the user increases, and analyzes that the attention degree of the gaze of the user increases as the moving speed of the gaze decreases (refer to a section D1 in which the moving speed of the gaze is low). As described above, the analysis unit 11 analyzes the attention degree of the gaze of the user with respect to the gaze data at each predetermined time (a time when the user performs observation or diagnostic interpretation with respect to the image). Furthermore, in FIG. 3, the analysis unit 11 analyzes the moving speed of the gaze of the user, and thus, analyzes the attention degree of the gaze of the user, but is not limited thereto, and may analyze the attention degree of the gaze by detection any one of the moving distance of the gaze of the user within the predetermined time and the residence time of the gaze of the user prescribed area.

Returning to FIG. 2, Step S103 and the subsequence will be continuously described.

In Step S103, the setting unit 12 performs setting of assigning the important degree according to the attention degree that is analyzed by the analysis unit 11 at each predetermined time interval with respect to the speech data that is synchronized with the gaze data to be recorded in the recording unit 14. After Step S103, the information processing apparatus 10 proceeds to Step S104 described below.

FIG. 4A is a diagram schematically illustrating a setting method of assigning the important degree to the speech data of the setting unit 12. In FIG. 4A, a horizontal axis represents a time, a vertical axis in (a) of FIG. 4A represents an attention degree, a vertical axis in (b) of FIG. 4A represents speech data (phonation), and a vertical axis in (c) of FIG. 4A represents an important degree. In addition, a curve L2 in (a) of FIG. 4A represents a time change in the attention degree, a curve L3 in (b) of FIG. 4 represents a time change in the speech data, and a curve L4 in (c) of FIG. 4A represents a time change in the important degree.

As illustrated in FIG. 4A, in the curve L2, the curve L3, and the curve L4, in a case where there is a change in the speech data, a possibility that the user phonates an important portion is low when the user does not gaze (since the gaze of the user is moved (changed)), and thus, it is possible to assume that the important degree is low. In contrast, as illustrated in FIG. 4A, in the curve L2, the curve L3, and the curve L4, in a case where there is a change in the speech data, a possibility that the user phonates an important portion is high when the attention degree of the gaze of the user is high (the section D1), and thus, it is possible to assume that the important degree is high.

Figure 4B:
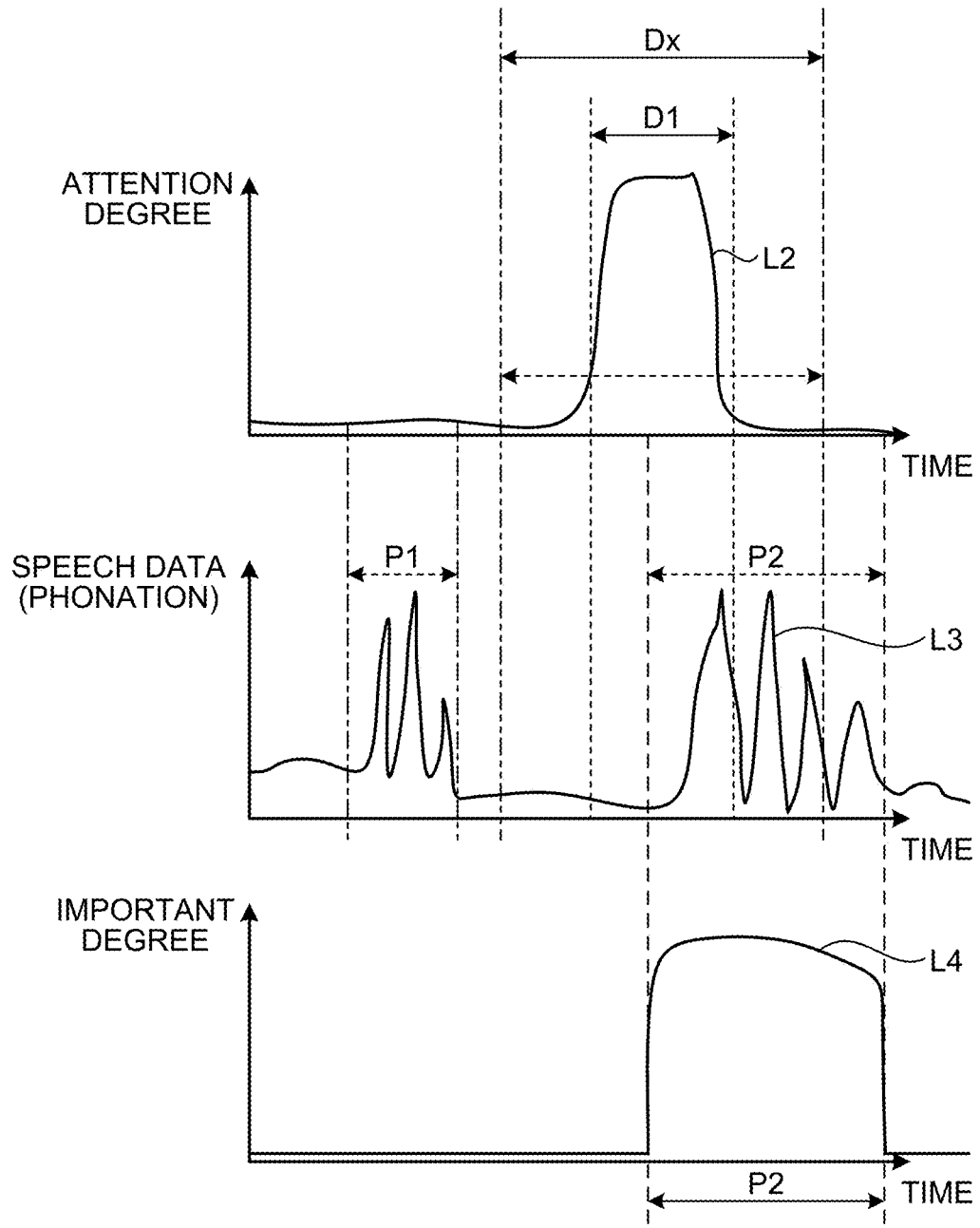
FIG. 4B is a diagram schematically illustrating another setting method of assigning the important degree to the speech data of the setting unit according to the first embodiment.

That is, the setting unit 12 performs setting of assigning the important degree according to the attention degree that is analyzed by the analysis unit 11 at each predetermined time interval with respect to the speech data to be recorded in the recording unit 14. Specifically, as illustrated in FIGS. 4A and 4B, the setting unit 12 performs setting of assigning a high important degree (for example, a number, a time when the gaze stays, a symbol indicating the size, and the like) with respect to the speech data of the section D1 analyzed by the analysis unit 11 that the attention degree is high to be recorded in the recording unit 14. At this time, in a case where there is a delay period dl of a gap between the section D1 analyzed by the analysis unit 11 that the attention degree is high and a phonation section D2 of the speech data, the setting unit 12 performs setting of assigning a high important degree to a phonation section including the phonation section D2 (for example, a section of approximately 1 seconds) in the vicinity of the speech data corresponding to the section D1 analyzed by the analysis unit 11 that the attention degree is high to be recorded in the recording unit 14.

Furthermore, in the first embodiment, calibration processing may be performed in which a time lag between the attention degree and the phonation (the pronunciation) of the user is calculated in advance (calibration data), and the gap between the attention degree and the phonation (the pronunciation) of the user is corrected on the basis of a calculation result.

In addition, in FIG. 4A, a delay time is provided between the section D1 and the phonation section D2 by focusing on a time gap between the attention degree of the gaze data and speaking data, but as a modification example of FIG. 4A, the setting unit 12 may set a period in which the important degree of the speech data is high by providing a margin before and after the section in which the attention degree of the gaze data is high. That is, the setting unit 12 may set a start time of the phonation section D2 to be earlier than a start time of the section D1, and an end time of the phonation section D2 to be later than an end time of the section D1.

In addition, in FIG. 4A, the setting unit 12 sets the temporal section D1 according to the attention degree, and sets the important degree of the speech data in consideration of the temporal section D1 that is set and the delay period dl. Furthermore, the setting unit 12 may combine data of the attention degree, and a function of detecting speaking together. Specifically, the setting unit 12 may specify a speaking period in which the speech data is spoken (may have the function of a speaking detection unit (not illustrated)). In this case, as illustrated in FIG. 4B, the setting unit 12 sets a window section Dx on the basis of the section D1 in which the attention degree is high. Then, the setting unit 12 detects (specifies) a speaking section (the speaking period) in which the user speaks, specifically, speaking sections P1 and P2 with respect to the speech data that is input. Here, in the speaking sections P1 and P2, the window section Dx based on the attention degree that is analyzed by the analysis unit 11 and a largely overlapping section (for example, a speaking period of the highest time correlation), specifically, the largely overlapping section is the speaking section P2, and thus, the setting unit 12 sets a high important degree to the speech data in the speaking section P2. That is, the setting unit 12 sets the important degree in consideration of both of the period in which the attention degree is high and a start and end section of the speaking section P2. More specifically, the setting unit 12 assigns the speaking section P2 (period) of the speech data in which the user speaks at a time within the section D1 (period) analyzed by the analysis unit 11 that the attention degree is high, as an important period to be recorded in the recording unit 14. In this case, the setting unit 12 assigns a higher important degree to the speech data as the attention degree increases to be recorded in the recording unit 14. Further, in a case where the user speaks at a time of a period analyzed by the analysis unit 11 that the attention degree is high, the setting unit 12 may assign the important degree to the speech data that is spoken by the user at the time of the period to be recorded in the recording unit 14.

Returning to FIG. 2, Step S104 and the subsequence will be continuously described.

In Step S104, the generating unit 13 generates the gaze mapping data in which the attention degree that is analyzed by the analysis unit 11 is associated with the image corresponding to the image data.

Subsequently, the display controller 15 superimposes the gaze mapping data that is generated by the generating unit 13 with the image corresponding to the image data, and outputs the gaze mapping data to the external display unit 20 (Step S105). After Step S105, the information processing apparatus 10 ends this processing.

FIG. 5 is a diagram schematically illustrating an example of the image that is displayed on the display unit 20. As illustrated in FIG. 5, the display controller 15 allows the display unit 20 to display a gaze mapping image P1 superimposed on the gaze mapping data that is generated by the generating unit 13, on the image corresponding to the image data. In FIG. 5, the gaze mapping image P1 of the heat maps M1 to M5 including more contour lines as the attention degree of the gaze increases is displayed on the display unit 20.

FIG. 6 is a diagram schematically illustrating another example of the image that is displayed on the display unit 20. As illustrated in FIG. 6, the display controller 15 allows the display unit 20 to display a gaze mapping image P2 superimposed on the gaze mapping data that is generated by the generating unit 13, on the image corresponding to the image data. In FIG. 6, the gaze mapping image P2 on which marks M11 to M15 of the attention degree including a larger circular area as the attention degree of the gaze increases are superimposed is displayed on the display unit 20. Further, the display controller 15 allows the display unit 20 to display a locus K1 of the gaze of the user and the order of the attention degree in numbers. Furthermore, in FIG. 6, the display controller 15 may allow the display unit 20 to display character information in which the speech data that is output by the user in the period (the time) of each attention degree is converted by using a known character conversion technology in the vicinity of or to be superimposed on the marks M11 to M15.

According to the first embodiment described above, the setting unit 12 performs setting of assigning the important degree according to the attention degree that is analyzed by the analysis unit 11 at each predetermined time interval with respect to the speech data that is input externally to be recorded in the recording unit 14, and thus, it is possible to understand which period of the speech data is important.

In addition, according to the first embodiment, the generating unit 13 generates the gaze mapping data in which the attention degree that is analyzed by the analysis unit 11, and coordinate information of the attention degree are associated with the image corresponding to the image data that is input externally, and thus, it is possible for the user to intuitively understand an important position on the image.

In addition, according to the first embodiment, the recording unit 14 records the speech data by assigning the important degree with the setting unit 12, and thus, it is possible to easily acquire learning data at the time of learning a correspondence relationship between the image data and the speech based on gaze mapping that is used in machine learning such as deep learning.

In addition, according to the first embodiment, the setting unit 12 assigns the period of the speech data in which the user speaks at the time of the section (the period) analyzed by the analysis unit 11 that the attention degree is high, as the important period to be recorded in the recording unit 14, and thus, the period can be recorded in the recording unit 14 by being distinguished from a section of the other speech data.

In addition, according to the first embodiment, the setting unit 12 assigns a higher important degree with respect to the speech data as the attention degree that is analyzed by the analysis unit 11 increases to be recorded in the recording unit 14, and thus, it is possible to relatively understand the important degree of each of the sections of the speech data.

In addition, according to the first embodiment, in a case where the user speaks at the time of the period analyzed by analysis unit 11 that the attention degree is high, the setting unit 12 assigns the important degree to the speech data that is spoken by the user at the time of the period to be recorded in the recording unit 14, and thus, even in a case where the attention degree is simply high, a low important degree is assigned with respect to a period in which there is no speech data, and thus, it is possible to perform adaptive learning according to the important degree at the time of learning the correspondence relationship between the image data and the speech based on the gaze mapping that is used in the machine learning such as deep learning.

Modification Example of First Embodiment

Next, a modification example of the first embodiment of the present disclosure will be described. In the first embodiment described above, the setting unit 12 assigns the important degree according to the attention degree that is analyzed by the analysis unit 11 to the speech data to be recorded in the recording unit 14, but in the modification example of the first embodiment, the setting unit 12 assigns the important degree at each predetermined time interval to the speech data, on the basis of the gaze mapping data that is generated by the generating unit 13 to be recorded in the recording unit 14. Hereinafter, the configuration of an information processing system according to the modification example of the first embodiment will be described, and then, processing that is executed by the information processing apparatus according to the modification example of the first embodiment will be described. Furthermore, the same reference numerals will be applied to the same configurations as those of the information processing system 1 according to the first embodiment described above, and the detailed description thereof will be omitted.

Configuration of Information Processing System

Figure 7:
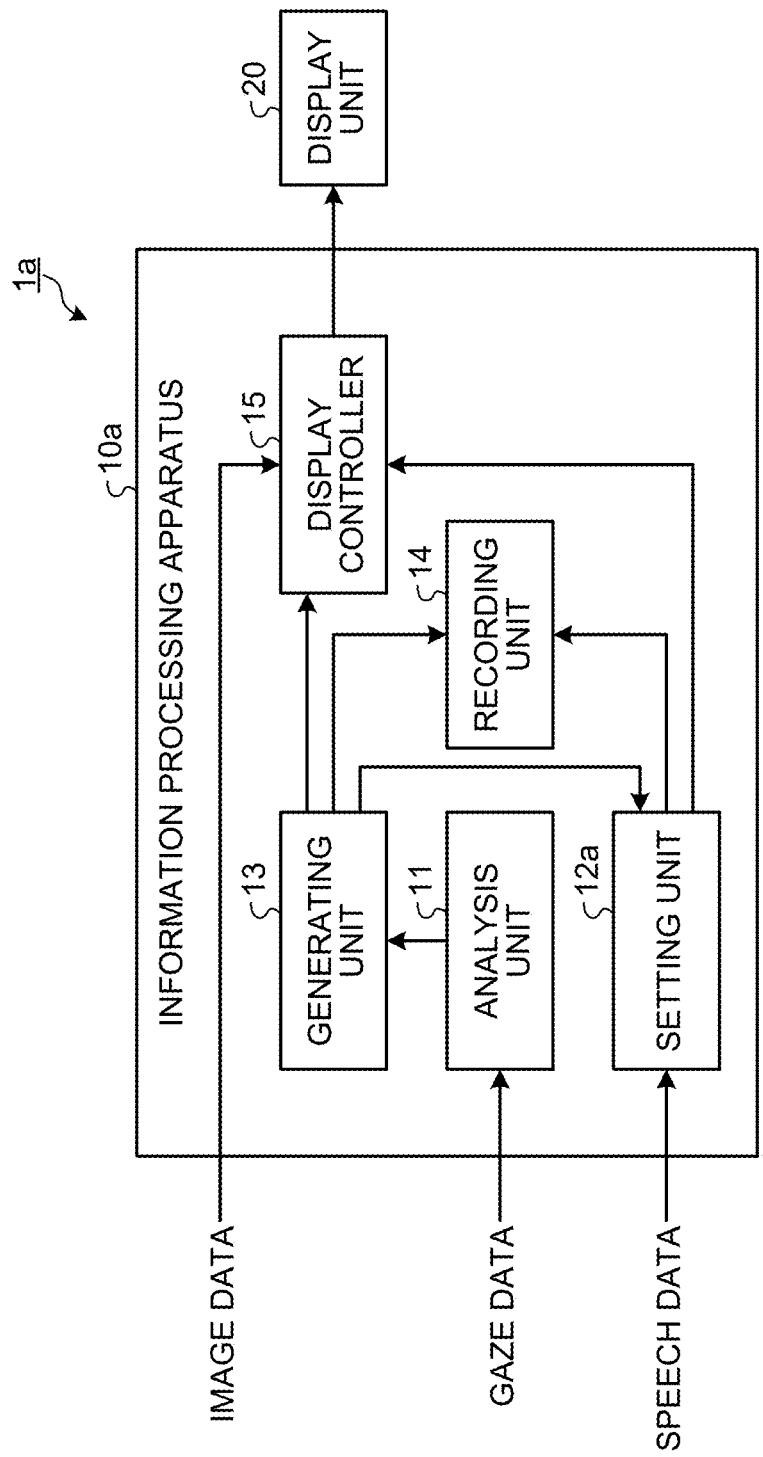
FIG. 7 is a block diagram illustrating a functional configuration of an information processing system according to a modification example of the first embodiment.

FIG. 7 is a block diagram illustrating a functional configuration of the information processing system according to the modification example of the first embodiment. An information processing system 1a illustrated in FIG. 7 includes an information processing apparatus 10a instead of the information processing apparatus 10 according to the first embodiment described above. The information processing apparatus 10a includes a setting unit 12a instead of the setting unit 12 according to the first embodiment described above.

The setting unit 12a assigns the important degree to the speech data at each predetermined time interval, on the basis of the gaze mapping data that is generated by the generating unit 13 to be recorded in the recording unit 14.

Processing of Information Processing Apparatus

Figure 8:
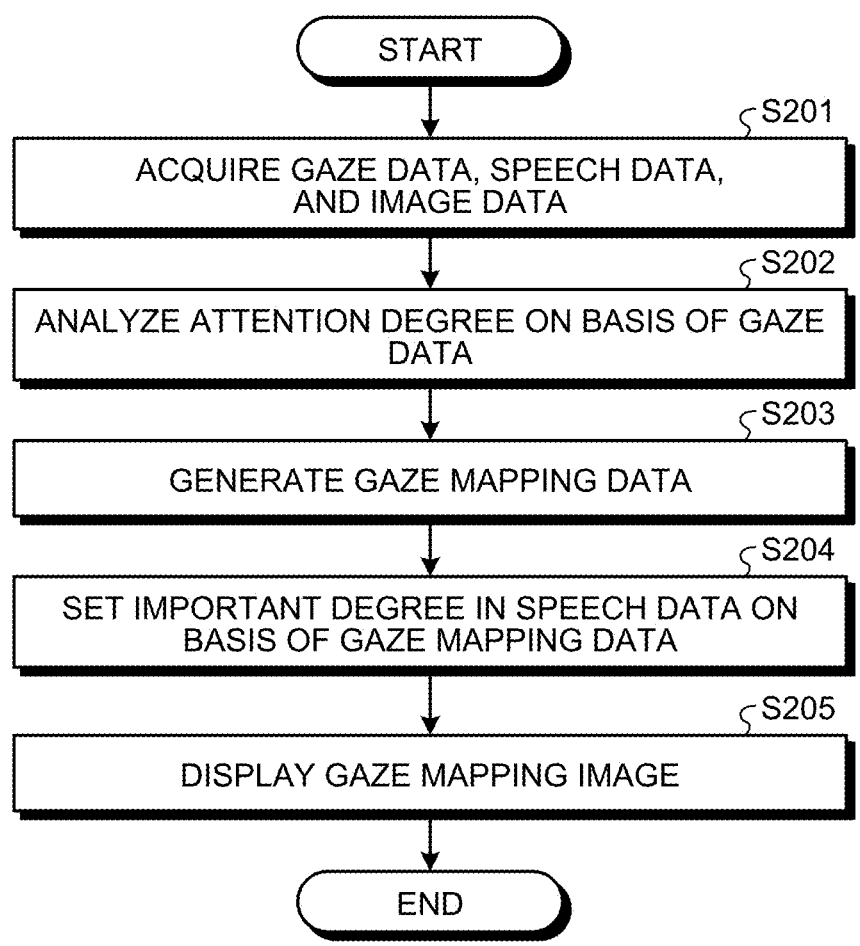
FIG. 8 is a flowchart illustrating an outline of processing that is executed by an information processing apparatus according to the modification example of the first embodiment.

Next, processing that is executed by the information processing apparatus 10a will be described. FIG. 8 is a flowchart illustrating the outline of the processing that is executed by the information processing apparatus 10a. In FIG. 8, Step S201 and Step S202 respectively correspond to Step S101 and Step S102 of FIG. 2 described above. In addition, in FIG. 8, Step S203 corresponds to Step S104 of FIG. 2 described above.

In Step S204, the setting unit 12 performs setting of assigning the important degree according to the attention degree at each predetermined time interval to the speech data, on the basis of the gaze mapping data in which the attention degree of the user that is generated by the generating unit 13 is associated with the image to be recorded in the recording unit 14. After Step S204, the information processing apparatus 10a proceeds to Step S205. Step S205 corresponds to Step S105 of FIG. 2 described above.

According to the modification example of the first embodiment described above, the setting unit 12 performs setting of assigning the important degree according to the attention degree at each predetermined time interval to the speech data, on the basis of gaze mapping data in which the attention degree of the user that is generated by the generating unit 13 is associated with the image to be recorded in the recording unit 14, and thus, it is possible to understand which period of the speech data is important.

Second Embodiment

Next, a second embodiment of the present disclosure will be described. In the first embodiment, each of the gaze data and the speech data is input externally, but in the second embodiment, the gaze data and the speech data are generated. Hereinafter, the configuration of an information processing apparatus according to the second embodiment will be described, and then, processing that is executed by the information processing apparatus according to the second embodiment will be described. Furthermore, the same reference numerals will be applied to the same configurations as those of the information processing system 1 according to the first embodiment described above, and the detailed description will be suitably omitted.

Configuration of Information Processing Apparatus

Figure 9:
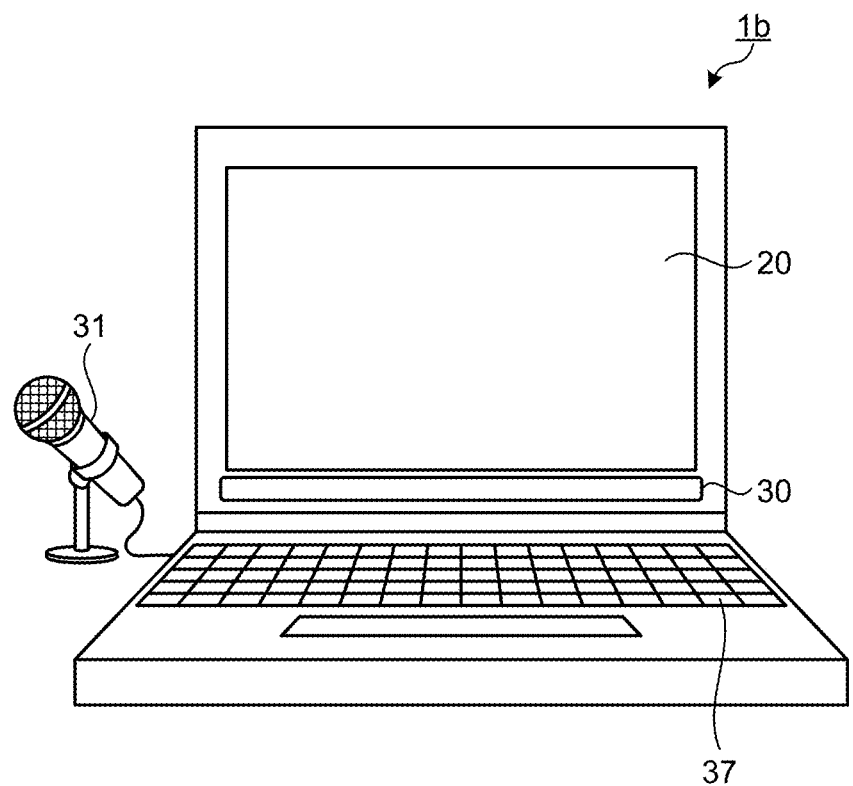
FIG. 9 is a schematic view illustrating a configuration of an information processing apparatus according to a second embodiment.
Figure 10:
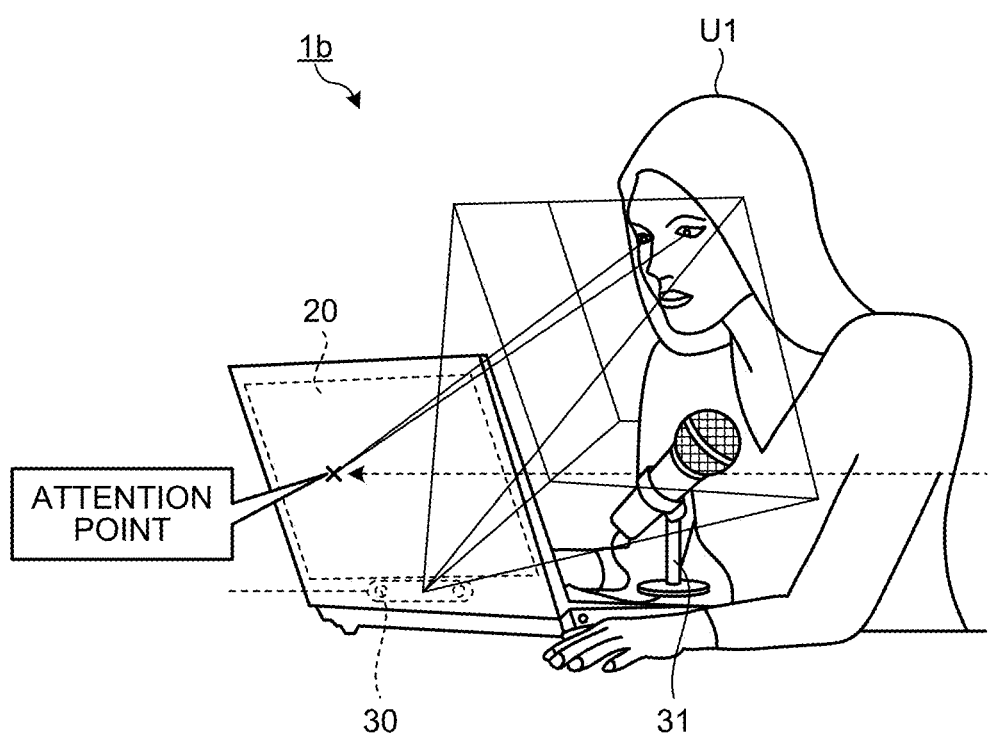
FIG. 10 is a schematic view illustrating a configuration of an information processing apparatus according to a second embodiment.
Figure 11:
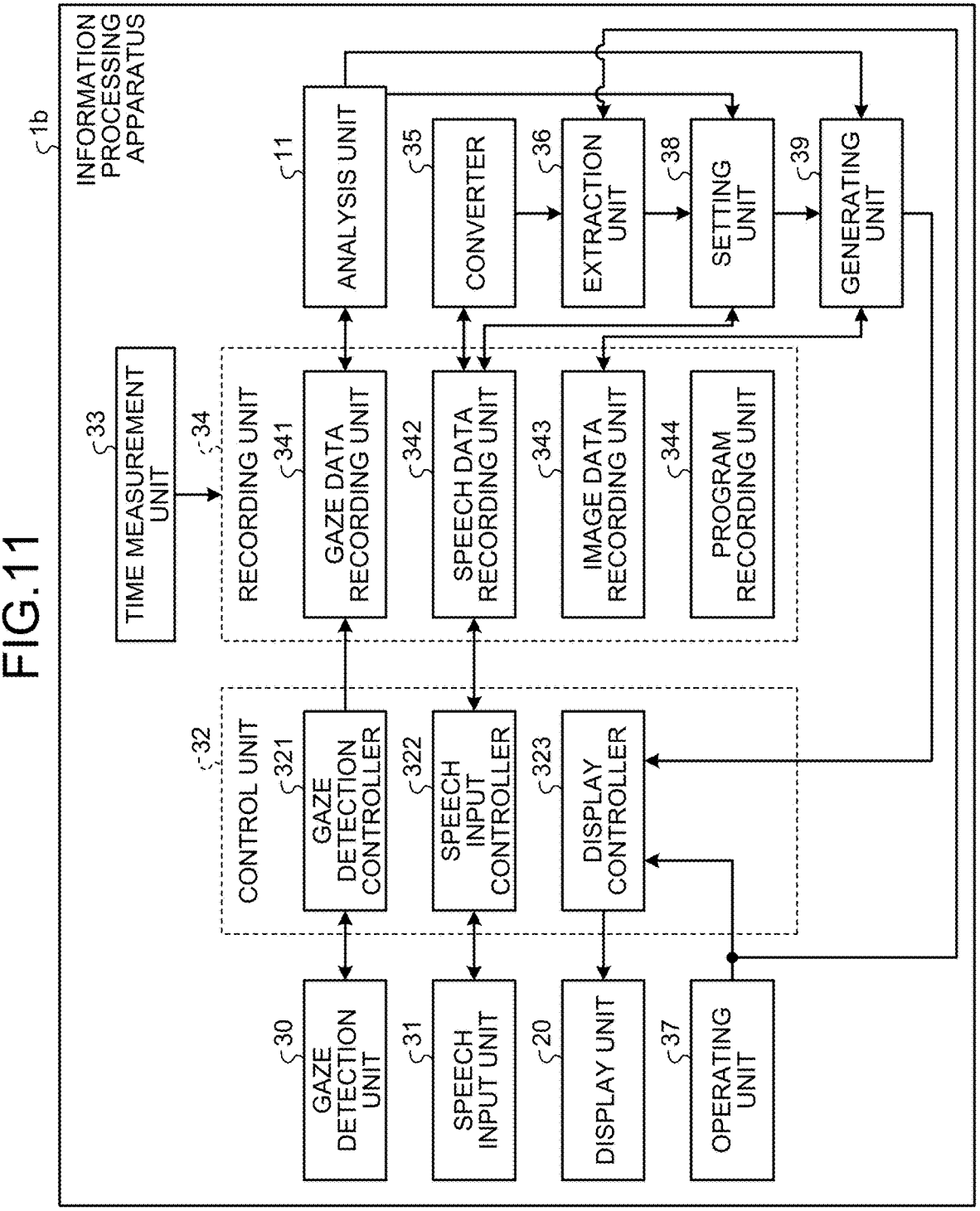
FIG. 11 is a block diagram illustrating a functional configuration of the information processing apparatus according to the second embodiment.

FIG. 9 is a schematic view illustrating the configuration of the information processing apparatus according to the second embodiment. FIG. 10 is a schematic view illustrating the configuration of the information processing apparatus according to the second embodiment. FIG. 11 is a block diagram illustrating a functional configuration of the information processing apparatus according to the second embodiment.

An information processing apparatus 1b illustrated in FIG. 9 to FIG. 11 includes the analysis unit 11, the display unit 20, a gaze detection unit 30, a speech input unit 31, a control unit 32, a time measurement unit 33, a recording unit 34, a converter 35, an extraction unit 36, an operating unit 37, a setting unit 38, and a generating unit 39.

The gaze detection unit 30 is configured by using an LED light source that emits a near infrared ray, and an optical sensor (for example, a CMOS, a CCD, or the like) that captures a pupil point and a reflex point on the cornea. The gaze detection unit 30 is provided on a side surface of a housing of the information processing apparatus 1b on which the display unit 20 is visible to a user U1 (refer to FIG. 9 and FIG. 10). The gaze detection unit 30 generates the gaze data in which the gaze of the user U1 with respect to the image that is displayed on the display unit 20 is detected, and outputs the gaze data to the control unit 32, under the control of the control unit 32. Specifically, the gaze detection unit 30 generates the gaze data by irradiating the cornea of the user U1 with a near infrared ray from the LED light source or the like, and by capturing the pupil point and the reflex point on the cornea of the user U1 with the optical sensor, under the control of the control unit 32. Then, the gaze detection unit 30 may generate the gaze data of a predetermined time by continuously calculating the gaze of the user from the pattern of the pupil point and the reflex point of the user U1, on the basis of an analysis result analyzed by performing image processing or the like with respect to data that is generated by the optical sensor, and outputs the gaze data to a gaze detection controller 321 described below, under the control of the control unit 32. Furthermore, the gaze detection unit 30 may generate the gaze data in which the gaze of the user U1 is detected by simply detecting the pupil of the user U1 only with the optical sensor by using known pattern matching, or may generate gaze data by detecting the gaze of the user U1 by using other sensors or other known technologies.

The speech input unit 31 is configured by using a microphone to which a speech is input, and a speech codec that converts the speech of which the input is received by the microphone into digital speech data, and outputs the speech data to the control unit 32 by amplifying the speech data. The speech input unit 31 generates the speech data by receiving the input of the speech of the user U1, under the control of the control unit 32, and outputs the speech data to the control unit 32. Furthermore, the speech input unit 31 may be provided with a speech output function by including a speaker or the like that is capable of outputting a speech, in addition to the input of the speech.

The control unit 32 is configured by using a CPU, an FPGA, a GPU, and the like, and controls the gaze detection unit 30, the speech input unit 31, and the display unit 20. The control unit 32 includes the gaze detection controller 321, a speech input controller 322, and a display controller 323.

The gaze detection controller 321 controls the gaze detection unit 30. Specifically, the gaze detection controller 321 allows the gaze detection unit 30 to generate the gaze data by irradiating the user U1 with a near infrared ray at each predetermined timing, and by capturing the pupil of the user U1. In addition, the gaze detection controller 321 performs various pieces of image processing with respect to the gaze data that is input from the gaze detection unit 30, and outputs the gaze data to the recording unit 34.

The speech input controller 322 controls the speech input unit 31, performs various pieces of processing, for example, gain-up processing, noise reduction processing, or the like with respect to the speech data that is input from the speech input unit 31, and outputs the speech data to the recording unit 34.

The display controller 323 controls a display mode of the display unit 20. The display controller 323 allows the display unit 20 to display an image corresponding to the image data that is recorded in the recording unit 34 or the gaze mapping image corresponding to the gaze mapping data that is generated by the generating unit 39.

The time measurement unit 33 is configured by using a timer, a clock generator, or the like, and applies time information to the gaze data that is generated by the gaze detection unit 30, the speech data that is generated by the speech input unit 31, and the like.

The recording unit 34 is configured by using a volatile memory, a non-volatile memory, a recording medium, and the like, and records various kinds of information relevant to the information processing apparatus 1b. The recording unit 34 includes a gaze data recording unit 341, a speech data recording unit 342, an image data recording unit 343, and a program recording unit 344.

The gaze data recording unit 341 records the gaze data that is input from the gaze detection controller 321, and outputs the gaze data to the analysis unit 11.

The speech data recording unit 342 records the speech data that is input from the speech input controller 322, and outputs the speech data to the converter 35.

The image data recording unit 343 records a plurality of image data. The plurality of image data are data that is input externally of the information processing apparatus 1b, or data that is captured by an external imaging device in a recording medium.

The program recording unit 344 records various programs that are executed by the information processing apparatus 1b, data that is used during the execution of various programs (for example, dictionary information or text conversion dictionary information), and processing data during the execution of various programs.

The converter 35 performs known text conversion processing with respect to the speech data, and thus, converts the speech data into the character information (text data), and outputs the character information to the extraction unit 36.

Furthermore, the character conversion of the speech may not be performed at this time point, and in that case, the important degree may be set as speech information, and then, may be converted into the character information.

The extraction unit 36 extracts a character or a word (a keyword) corresponding to an instruction signal that is input from the operating unit 37 described below, from the character information that is converted by the converter 35, and outputs the extraction result to the setting unit 38. Furthermore, in a case where the instruction signal is not input from the operating unit 37 described below, the extraction unit 36 outputs the character information as is input from the converter 35 to the setting unit 38.

The operating unit 37 is configured by using a mouse, a keyboard, a touch panel, various switches, and the like, receives the input of the operation of the user U1, and outputs operation contents of which the input is received to the control unit 32.

The setting unit 38 assigns the important degree and the character information that is converted into the converter 35 to the speech data that is associated with a time axis identical to that of the gaze data, on the basis of the attention degree that is analyzed by the analysis unit 11 at each predetermined time interval and the character information that is extracted by the extraction unit 36, to be recorded in the recording unit 34.

The generating unit 39 generates the gaze mapping data in which the attention degree that is analyzed by the analysis unit 11 and the character information that is converted into the converter 35 are associated with the image corresponding to the image data that is displayed on the display unit 20, and outputs the gaze mapping data to the image data recording unit 343 or the display controller 323.

Processing of Information Processing Apparatus

Figure 12:
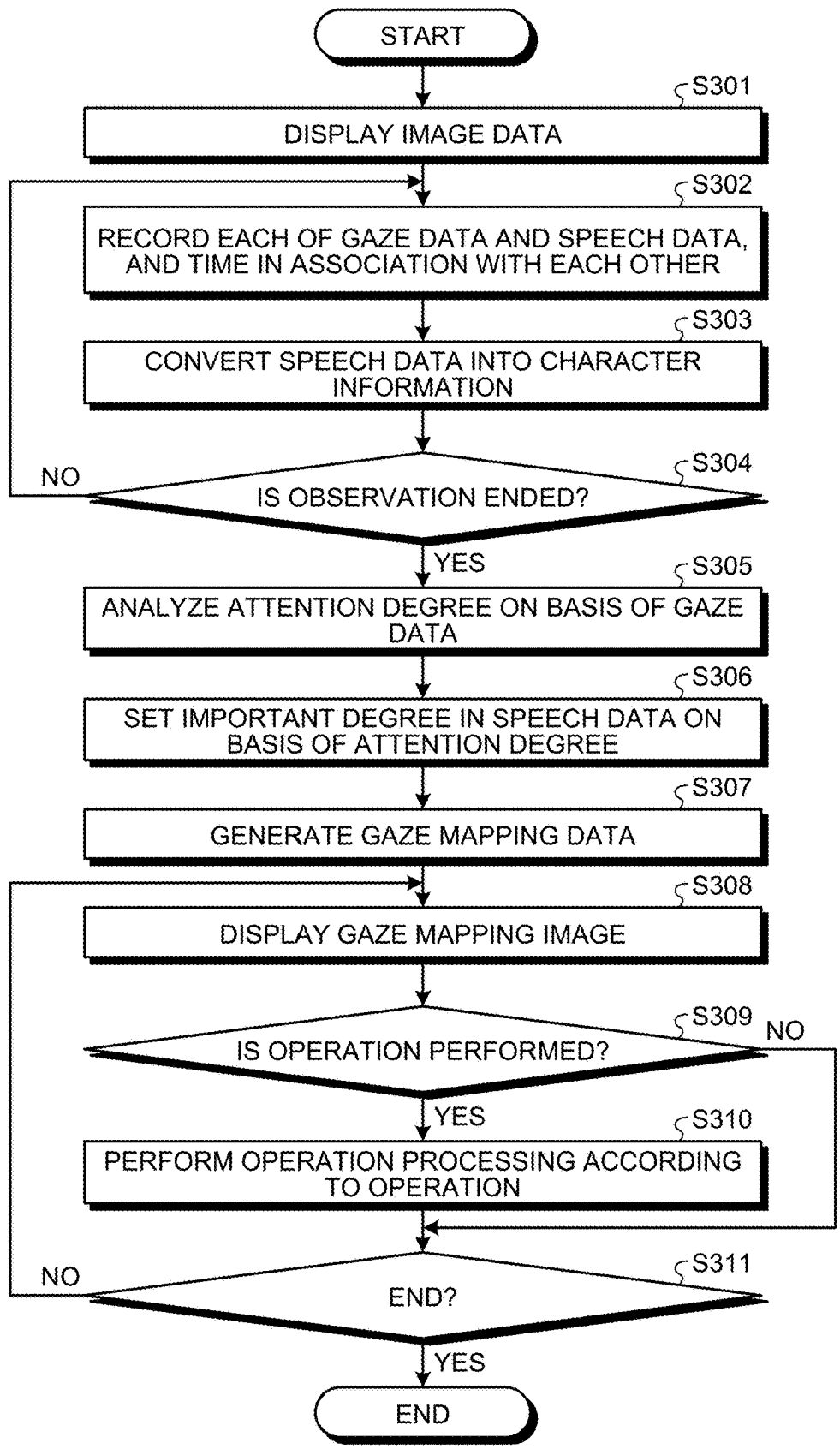
FIG. 12 is a flowchart illustrating an outline of processing that is executed by the information processing apparatus.

Next, processing that is executed by the information processing apparatus 1b will be described. FIG. 12 is a flowchart illustrating the outline of the processing that is executed by the information processing apparatus 1b.

As illustrated in FIG. 12, first, the display controller 323 allows the display unit 20 to display the image corresponding to the image data that is recorded in the image data recording unit 343 (Step S301). In this case, the display controller 323 allows the display unit 20 to display the image corresponding to the image data that is selected according to the operation of the operating unit 37.

Subsequently, the control unit 32 associates each of the gaze data that is generated by the gaze detection unit 30 and the speech data that is generated by the speech input unit 31 with the time that is measured by the time measurement unit 33 to be recorded in the gaze data recording unit 341 and the speech data recording unit 342 (Step S302).

After that, the converter 35 converts the speech data that is recorded in the speech data recording unit 342 into the character information (Step S303). Furthermore, such a step may be performed after S306 described below.

Subsequently, in a case where an instruction signal of ending the observation of the image that is displayed on the display unit 20 is input from the operating unit 37 (Step S304: Yes), the information processing apparatus 1b proceeds to Step S305 described below. In contrast, in a case where the instruction signal of ending the observation of the image that is displayed on the display unit 20 is not input from the operating unit 37 (Step S304: No), the information processing apparatus 1b returns to Step S302.

Step S305 corresponds to Step S102 of FIG. 2 described above. After Step S305, the information processing apparatus 1b proceeds to Step S306 described below.

In Step S306, the setting unit 38 assigns the important degree and the character information that is converted by the converter 35 to the speech data that is associated with a time axis identical to that of the gaze data, on the basis of the attention degree that is analyzed by the analysis unit 11 at each predetermined time interval and the character information that is extracted by the extraction unit 36 to be recorded in the recording unit 34. In this case, the setting unit 38 performs weighting of the important degree of the speech data corresponding to the character information that is extracted by the extraction unit 36 to be recorded in the recording unit 34. For example, the setting unit 38 assigns a value obtained by multiplying a coefficient based on the character information that is extracted by the extraction unit 36 and the attention degree together to the speech data, as the important degree to be recorded in the recording unit 34.

Subsequently, the generating unit 39 generates gaze mapping data in which the attention degree that is analyzed by the analysis unit 11 and the character information that is converted by the converter 35 are associated with the image corresponding to the image data that is displayed on the display unit 20 (Step S307).

Subsequently, the display controller 323 allows the display unit 20 to display the gaze mapping image corresponding to the gaze mapping data that is generated by the generating unit 39 (Step S308).

Figure 13:
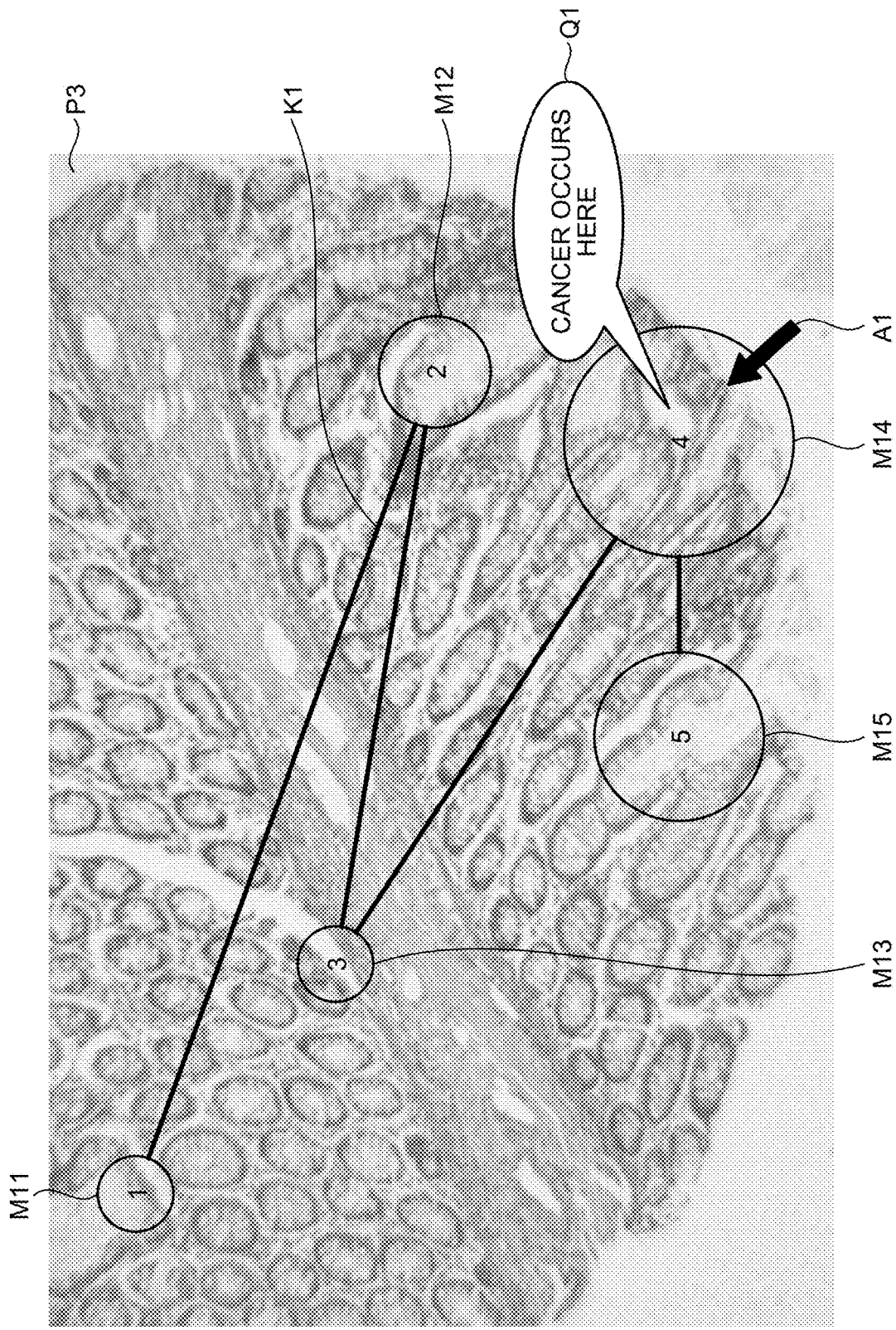
FIG. 13 is a diagram illustrating an example of a gaze mapping image that is displayed on a display unit according to the second embodiment.

FIG. 13 is a diagram illustrating an example of the gaze mapping image that is displayed on the display unit 20. As illustrated in FIG. 13, the display controller 323 allows the display unit 20 to display a gaze mapping image P3 corresponding to the gaze mapping data that is generated by the generating unit 39. The marks M11 to M15 corresponding to the attention area of the gaze and the locus K1 of the gaze are superimposed on the gaze mapping image P3, and the character information of the speech data that is output at the timing of the attention degree is associated with the gaze mapping image P3.

In addition, in the marks M11 to M15, the number indicates the order of the gaze of the user U1, and the size (the area) indicates the size of the attention degree. Further, in a case where the user U1 moves a cursor A1 to a desired position by operating the operating unit 37, for example, to the mark M14, character information Q1 that is associated with the mark M14, for example, "Cancer Occurs Here." is displayed. Furthermore, in FIG. 13, the display controller 323 allows the display unit 20 to display the character information, but for example, may output the speech data by converting the character information into a speech. Accordingly, the user U1 is capable of intuitively understanding an important speech contents and an area at which the user gazes. Further, it is possible to intuitively understand the locus of the gaze in the observation of the user U1.

Figure 14:
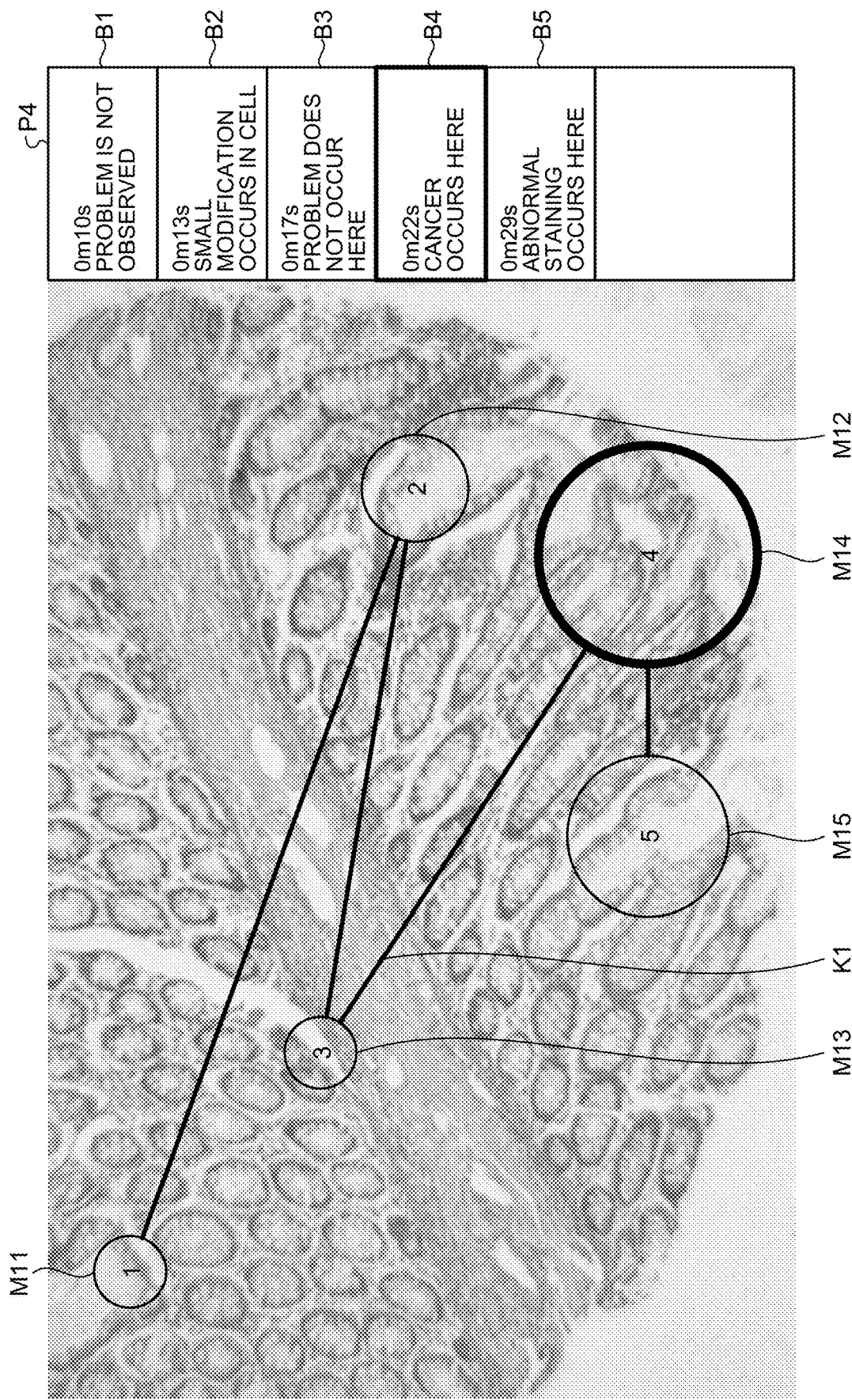
FIG. 14 is a diagram illustrating another example of the gaze mapping image that is displayed on the display unit according to the second embodiment.

FIG. 14 is a diagram illustrating another example of the gaze mapping image that is displayed on the display unit 20. As illustrated in FIG. 14, the display controller 323 allows the display unit 20 to display a gaze mapping image P4 corresponding to the gaze mapping data that is generated by the generating unit 39. Further, the display controller 323 allows the display unit 20 to display icons B1 to B5 in which the character information is associated with a time when the character information is pronounced. Further, the user U1 selects any one of the marks M11 to M15 by operating the operating unit 37, for example, selects the mark M14, the display controller 323 allows the display unit 20 to highlight-display the mark M14, and allows the display unit 20 to highlight-display the character information corresponding to the time of the mark M14, for example, the icon B4 (for example, to highlight-display or display a frame by a bold line). Accordingly, the user U1 is capable of intuitively understanding important speech contents and an area at which the user gazes, and of capable of intuitively understanding the contents at the time of being pronounced.

Returning to FIG. 12, Step S309 and the subsequence will be continuously described.

In Step S309, in a case where any one of the marks corresponding to a plurality of attention areas is operated by the operating unit 37 (Step S309: Yes), the control unit 32 executes operation processing according to the operation (Step S310). Specifically, the display controller 323 allows the display unit 20 to highlight-display the mark corresponding to the attention area that is selected by the operating unit 37 (for example, refer to FIG. 14). In addition, the speech input controller 322 allows the speech input unit 31 to play the speech data that is associated with an area having a high attention degree. After Step S310, the information processing apparatus 1b proceeds to Step S311 described below.

In Step S309, in a case where any one of the marks corresponding to the plurality of attention degree areas is not operated by the operating unit 37 (Step S309: No), the information processing apparatus 1b proceeds to Step S311 described below.

In Step S311, in a case where an instruction signal of instructing the end of the observation is input from the operating unit 37 (Step S311: Yes), the information processing apparatus 1b ends this processing. In contrast, in a case where the instruction signal of instructing the end of the observation is not input from the operating unit 37 (Step S311: No), the information processing apparatus 1b returns to Step S308 described above.

According to the second embodiment described above, the generating unit 39 generates the gaze mapping data in which the attention degree that is analyzed by the analysis unit 11 and the character information that is converted by the converter 35 are associated with the image corresponding to the image data that is displayed on the display unit 20, and thus, the user U1 is capable of intuitively understanding important speech contents and an area at which the user gazes, and of intuitively understanding the contents at the time of being pronounced.

In addition, according to the second embodiment, the display controller 323 allows the display unit 20 to display the gaze mapping image corresponding to the gaze mapping data that is generated by the generating unit 39, and thus, can be used in the confirmation of preventing the observation of the user with respect to the image from being missed, the confirmation of technical skill such as diagnostic interpretation of the user, and the education, the conference, and the like of the diagnostic interpretation, the observation, or the like with respect to other users.

Third Embodiment

Next, a third embodiment of the present disclosure will be described. In the second embodiment described above, only the information processing apparatus 1b is provided, but in the third embodiment, the information processing apparatus is incorporated in a part of the microscope system. Hereinafter, the configuration of a microscope system according to the third embodiment will be described, and then, processing that is executed by the microscope system according to the third embodiment will be described. Furthermore, the same reference numerals will be applied to the same configurations as those of the information processing apparatus 1b according to the second embodiment described above, and the detailed description will be suitably omitted.

Configuration of Microscope System

Figure 15:
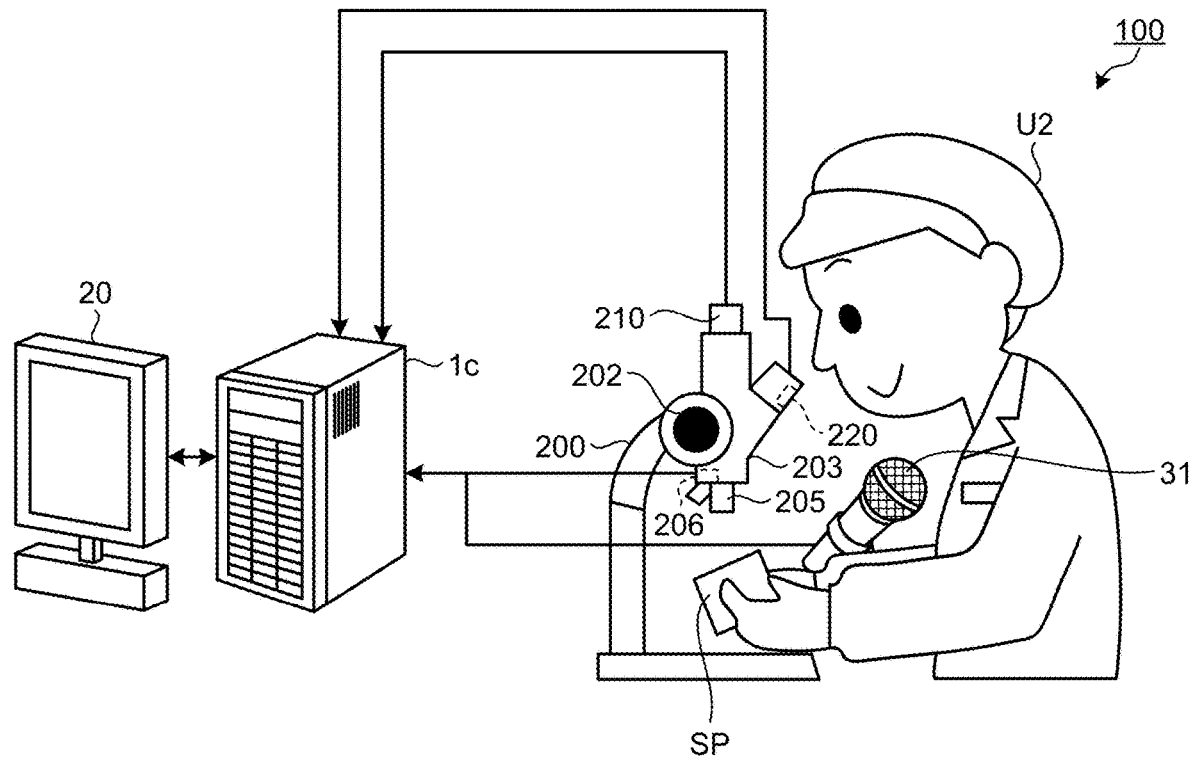
FIG. 15 is a schematic view illustrating a configuration of a microscope system according to a third embodiment.
Figure 16:
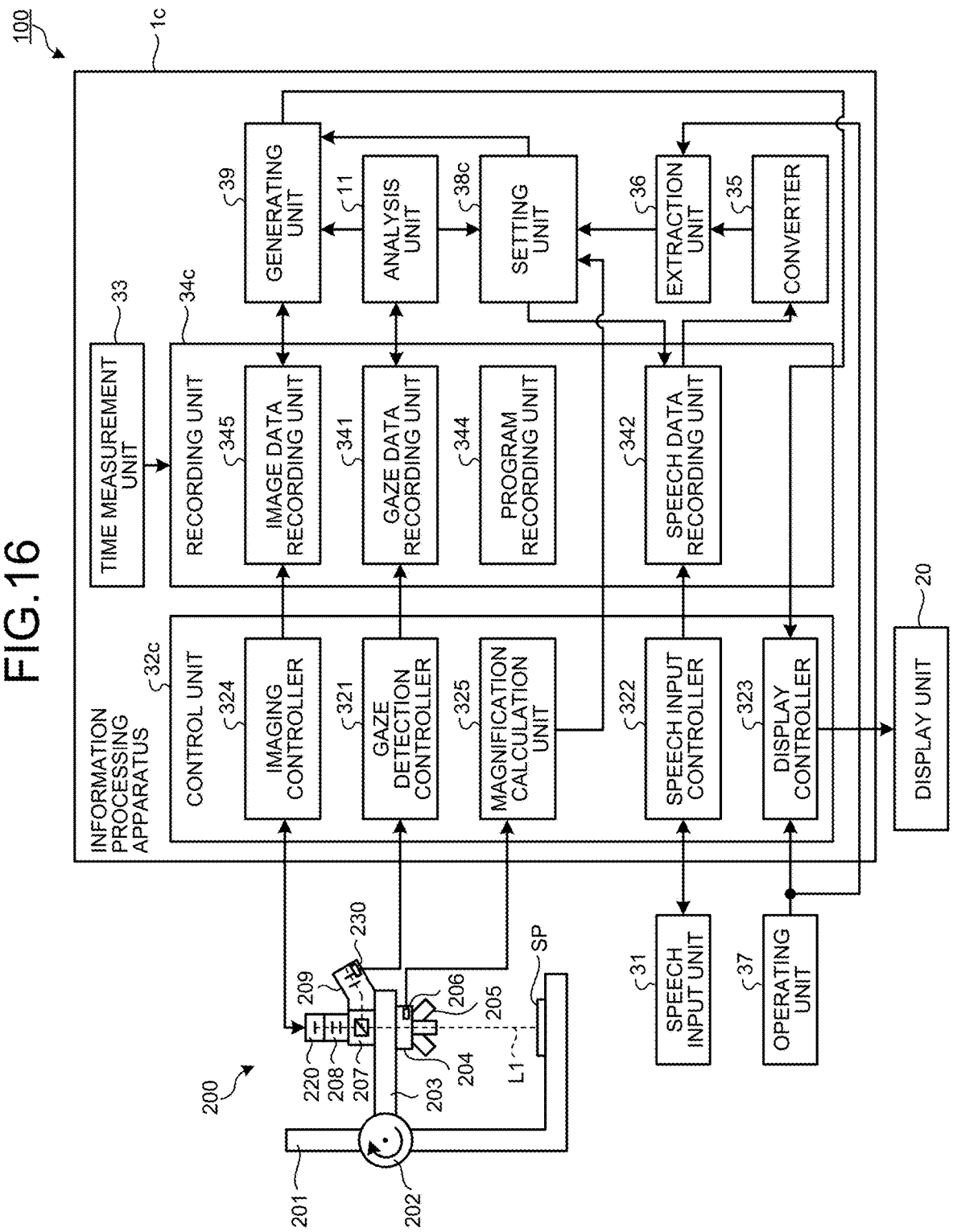
FIG. 16 is a block diagram illustrating a functional configuration of the microscope system according to the third embodiment.

FIG. 15 is a schematic view illustrating the configuration of the microscope system according to the third embodiment. FIG. 16 is a block diagram illustrating a functional configuration of the microscope system according to the third embodiment.

As illustrated in FIG. 15 and FIG. 16, a microscope system 100 includes an information processing apparatus 1c, a display unit 20, a speech input unit 31, an operating unit 37, a microscope 200, an imaging unit 210, and a gaze detection unit 220.

Configuration of Microscope

First, the configuration of the microscope 200 will be described.

The microscope 200 includes a main body portion 201, a rotation portion 202, an elevating portion 203, a revolver 204, an objective lens 205, a magnification detection unit 206, a lens barrel portion 207, a connection portion 208, and an eyepiece portion 209.

A specimen SP is mounted on the main body portion 201. The main body portion 201 is approximately in the shape of U, and the elevating portion 203 is connected to the main body portion 201 by using the rotation portion 202.

The rotation portion 202 is rotated according to the operation of a user U2, and thus, moves the elevating portion 203 in a vertical direction.

The elevating portion 203 is provided to be movable in the vertical direction with respect to the main body portion 201. In the elevating portion 203, the revolver 204 is connected to a surface on one end side, and the lens barrel portion 207 is connected to a surface on the other end side.

A plurality of objective lenses 205 having magnifications different from each other are connected to the revolver 204, and the revolver 204 is rotatably connected to the elevating portion 203 with respect to an optical axis L1. The revolver 204 arranges a desired objective lens 205 on the optical axis L1 according to the operation of a user U2. Furthermore, information indicating the magnification, for example, an IC chip or a label is attached to the plurality of objective lenses 205. Furthermore, a shape indicating the magnification may be provided in the objective lens 205, in addition to the IC chip or the label.

The magnification detection unit 206 detects the magnification of the objective lens 205 that is arranged on the optical axis L1, and outputs a detection result thereof to the information processing apparatus 1c. The magnification detection unit 206, for example, includes a unit detecting the position of the objective switching revolver 204.

The lens barrel portion 207 transmits a part of a subject image of the specimen SP that is formed by the objective lens 205 through the connection portion 208 to be reflected on the eyepiece portion 209. The lens barrel portion 207 includes a prism, a half mirror, a collimator lens, and the like inside.

In the connection portion 208, one end is connected to the lens barrel portion 207, and the other end is connected to the imaging unit 210.

The connection portion 208 guides the subject image of the specimen SP that is transmitted through the lens barrel portion 207 to the imaging unit 210. The connection portion 208 is configured by using a plurality of collimator lenses and tube lenses, and the like.

The eyepiece portion 209 forms an image by guiding the subject image that is reflected on the lens barrel portion 207. The eyepiece portion 209 is configured by using a plurality of collimator lenses and tube lenses, and the like.

Configuration of Imaging Unit

Next, the configuration of the imaging unit 210 will be described.

The imaging unit 210 generates the image data by receiving the subject image of the specimen SP that is formed by the connection portion 208, and outputs the image data to the information processing apparatus 1c. The imaging unit 210 is configured by using an image sensor such as a CMOS or a CCD, an image processing engine performing various pieces of image processing with respect to the image data, and the like.

Configuration of Gaze Detection Unit

Next, the configuration of the gaze detection unit 220 will be described.

The gaze detection unit 220 is provided inside or outside the eyepiece portion 209, generates the gaze data by detecting the gaze of the user U2, and outputs the gaze data to the information processing apparatus 1c. The gaze detection unit 220 is configured by using an LED light source that is provided inside the eyepiece portion 209, and emits a near infrared ray, an optical sensor that is provided inside the eyepiece portion 209, and captures the pupil point and the reflex point on the cornea (for example, a CMOS and a CCD). The gaze detection unit 220 irradiates the cornea of the user U2 with a near infrared ray from the LED light source or the like, the gaze data by capturing the pupil point and the reflex point on the cornea of the user U2 with the optical sensor, under the control of the information processing apparatus 1c. Then, the gaze detection unit 220 generates the gaze data by detecting the gaze of the user from the pattern of a pupil point and a reflex point of the user U2, and outputs the gaze data to the information processing apparatus 1c, on the basis of an analysis result analyzed by image processing or the like with respect to the data that is generated by the optical sensor, under the control of the information processing apparatus 1c.

Configuration of Information Processing Apparatus

Next, the configuration of the information processing apparatus 1c will be described.

The information processing apparatus 1c includes a control unit 32c, a recording unit 34c, and a setting unit 38c, instead of the control unit 32, the recording unit 34, and the setting unit 38 of the information processing apparatus 1b according to the second embodiment described above.

The control unit 32c is configured by using a CPU, an FPGA, a GPU, and the like, and controls the display unit 20, the speech input unit 31, the imaging unit 210, and the gaze detection unit 220. The control unit 32c further includes an imaging controller 324 and a magnification calculation unit 325, in addition to the gaze detection controller 321, the speech input controller 322, and the display controller 323 of the control unit 32 of the second embodiment described above.

The imaging controller 324 controls the operation of the imaging unit 210. The imaging controller 324 generates the image data by allowing the imaging unit 210 to sequentially perform capturing according to a predetermined frame rate. The imaging controller 324 performs image processing (for example, developing processing or the like) with respect to the image data that is input from the imaging unit 210, and outputs the image data to the recording unit 34c.

The magnification calculation unit 325 calculates an observation magnification of the current microscope 200, and outputs a calculation result to the setting unit 38c, on the basis of a detection result that is input from the magnification detection unit 206. For example, the magnification calculation unit 325 calculates the observation magnification of the current microscope 200 on the basis of the magnification of the objective lens 205 that is input from the magnification detection unit 206 and the magnification of the eyepiece portion 209.

The recording unit 34c is configured by using a volatile memory, a non-volatile memory, a recording medium, and the like. The recording unit 34c includes an image data recording unit 345, instead of the image data recording unit 343 according to the second embodiment described above. The image data recording unit 345 records the image data that is input from the imaging controller 324, and outputs the image data to the generating unit 39.

The setting unit 38c assigns the important degree and the character information that is converted by the converter 35 to the speech data that is associated with a time axis identical to the gaze data, on the basis of the attention degree that is analyzed by the analysis unit 11 at each predetermined time interval and a calculation result that is calculated by the magnification calculation unit 325 to be recorded in the recording unit 34c. Specifically, the setting unit 38c assigns a value obtained multiplied by a coefficient based on the calculation result that is calculated by the magnification calculation unit 325, to the attention degree that is analyzed by the analysis unit 11, as the important degree (for example, a numerical value) for each frame of the speech data to be recorded in the recording unit 34c. That is, the setting unit 38c performs processing increasing the important degree as the display magnification increases. The setting unit 38c is configured by using a CPU, an FPGA, a GPU, and the like.

Processing of Microscope System

Figure 17:
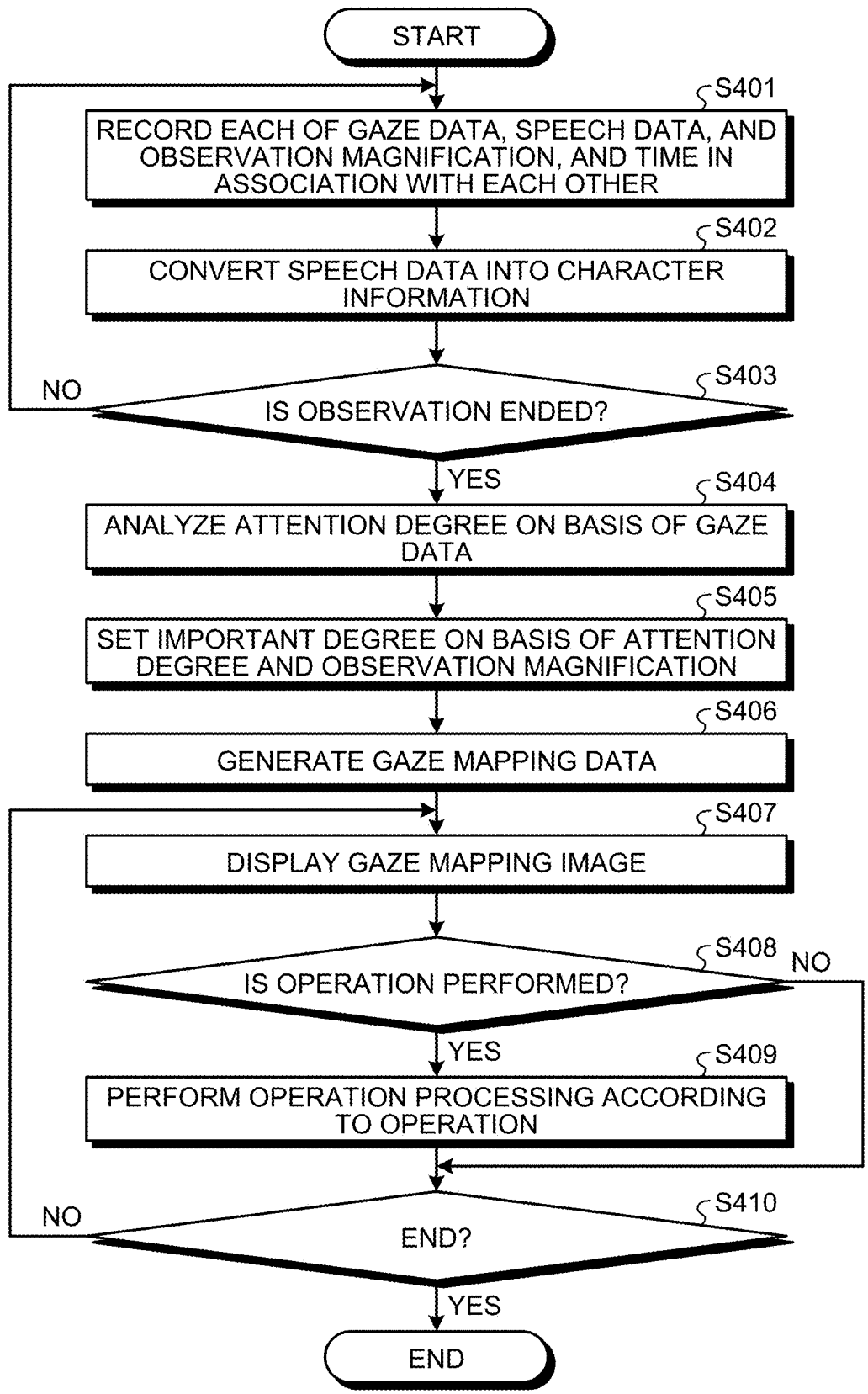
FIG. 17 is a flowchart illustrating an outline of processing that is executed by the microscope system according to the third embodiment.

Next, processing that is executed by the microscope system 100 will be described. FIG. 17 is a flowchart illustrating the outline of the processing that is executed by the microscope system 100.

As illustrated in FIG. 17, first, the control unit 32c associates each of the gaze data that is generated by the gaze detection unit 220, the speech data that is generated by the speech input unit 31, and the observation magnification that is calculated by the magnification calculation unit 325 with the time that is measured by the time measurement unit 33 to be recorded in the gaze data recording unit 341 and the speech data recording unit 342 (Step S401). After Step S401, the microscope system 100 proceeds to Step S402 described below.

Step S402 to Step S404 respectively correspond to Step S303 to Step S305 of FIG. 12 described above. After Step S404, the microscope system 100 proceeds to Step S405.

In Step S405, the setting unit 38c assigns the important degree and the character information that is converted by the converter 35 to the speech data associated with a time axis identical to that of the gaze data, on the basis of the attention degree that is analyzed by the analysis unit 11 at each predetermined time interval and the calculation result that is calculated by the magnification calculation unit 325 to be recorded in the recording unit 34c. After Step S405, the microscope system 100 proceeds to Step S406.

Step S406 to Step S410 respectively correspond to Step S307 to Step S311 of FIG. 12 described above.

According to the third embodiment described above, the setting unit 38c assigns the important degree and the character information that is converted by the converter 35 to the speech data that is associated with a time axis identical to that of the gaze data, on the basis of the attention degree that is analyzed by the analysis unit 11 and the calculation result that is calculated by the magnification calculation unit 325 to be recorded in the recording unit 34c, and thus, the important degree based on the observation magnification and the attention degree is assigned to the speech data, and therefore, it is possible to understand an important period of the speech data to which the observation contents and the attention degree are added.

Furthermore, in the third embodiment, the observation magnification that is calculated by the magnification calculation unit 325 is recorded in the recording unit 34c, but operation history of the user U2 may be recorded, and the important degree of the speech data may be assigned by further adding the operation history.

Fourth Embodiment

Next, a fourth embodiment of the present disclosure will be described. In the fourth embodiment, the information processing apparatus is incorporated in a part of an endoscope system. Hereinafter, a configuration of an endoscope system according to the fourth embodiment will be described, and then, processing that is executed by the endoscope system according to the fourth embodiment will be described. Furthermore, the same reference numerals will be applied to the same configurations as those of the information processing apparatus 1b according to the second embodiment described above, and the detailed description will be suitably omitted.

Configuration of Endoscope System

Figure 18:
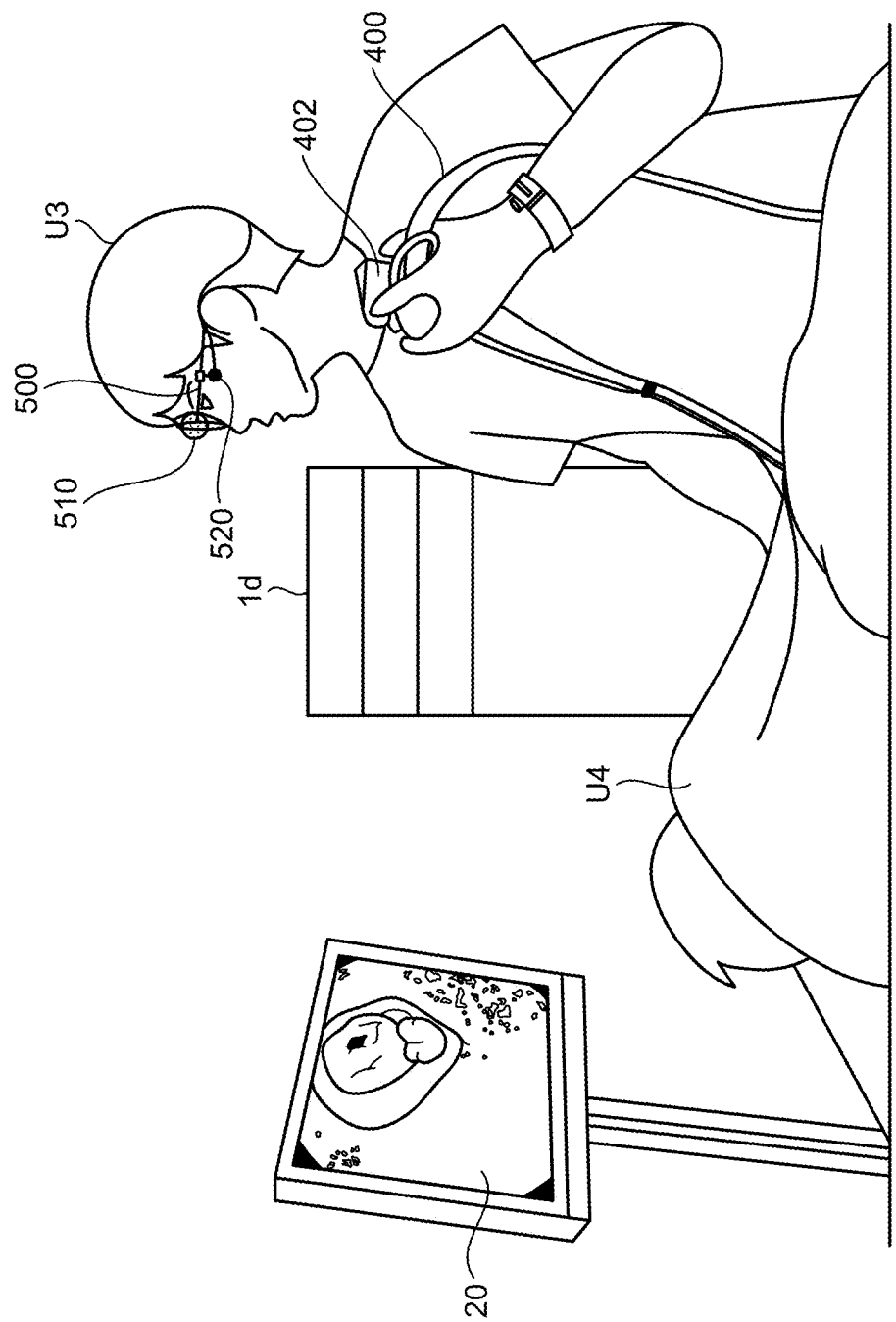
FIG. 18 is a schematic view illustrating a configuration of an endoscope system according to a fourth embodiment.
Figure 19:
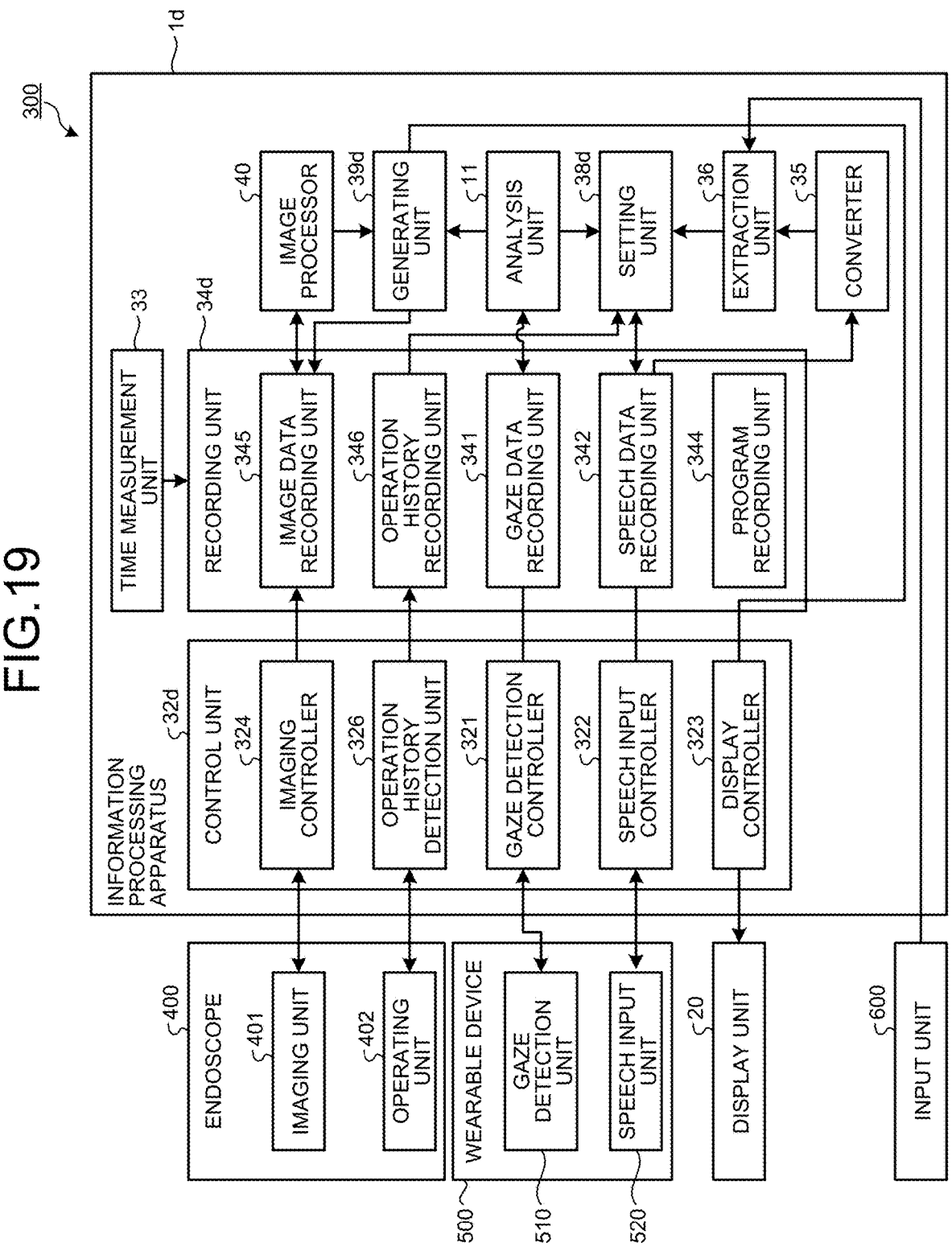
FIG. 19 is a block diagram illustrating a functional configuration of the endoscope system according to the fourth embodiment.

FIG. 18 is a schematic view illustrating the configuration of the endoscope system according to the fourth embodiment. FIG. 19 is a block diagram illustrating a functional configuration of the endoscope system according to the fourth embodiment.

An endoscope system 300 illustrated in FIG. 18 and FIG. 19 includes the display unit 20, an endoscope 400, a wearable device 500, an input unit 600, and an information processing apparatus 1d.

Configuration of Endoscope

First, the configuration of the endoscope 400 will be described.

The endoscope 400 generates the image data by being inserted into a subject U4 with a user U3 such as a medical doctor or an operator by capturing the inside of the subject U4, and outputs the image data to the information processing apparatus 1d. The endoscope 400 includes an imaging unit 401 and an operating unit 402.

The imaging unit 401 is provided on a tip end portion of an insertion portion of the endoscope 400. The imaging unit 401 generates the image data by capturing the inside of the subject U4, and outputs the image data to the information processing apparatus 1d, under the control of the information processing apparatus 1d. The imaging unit 401 is configured by using an optical system that is capable of changing the observation magnification, an image sensor such as a CMOS or a CCD that generates the image data by receiving the subject image that is formed by the optical system, and the like.

The operating unit 402 receives the input of various operations of the user U3, and outputs an operation signal according to the received various operations to the information processing apparatus 1d.

Configuration of Wearable Device

Next, the configuration of the wearable device 500 will be described.

The wearable device 500 is mounted on the user U3, detects the gaze of the user U3, and receives the input of the speech of the user U3. The wearable device 500 includes a gaze detection unit 510 and a speech input unit 520.

The gaze detection unit 510 is provided in the wearable device 500, generates the gaze data by detecting the attention degree of the gaze of the user U3, and outputs the gaze data to the information processing apparatus 1d. The gaze detection unit 510 has the same configuration as that of the gaze detection unit 220 according to the third embodiment described above, and thus, the detailed configuration will be omitted.

The speech input unit 520 is provided in the wearable device 500, generates the speech data by receiving the input of the speech of the user U3, and outputs the speech data to the information processing apparatus 1d. The speech input unit 520 is configured by using a microphone and the like.

Configuration of Input Unit

The configuration of the input unit 600 will be described.

The input unit 600 is configured by using a mouse, a keyboard, a touch panel, various switches, and the like. The input unit 600 receives the input of various operations of the user U3, and outputs the operation signal according to the received various operation to the information processing apparatus 1d.

Configuration of Information Processing Apparatus

Next, the configuration of the information processing apparatus 1d will be described.

The information processing apparatus 1d includes a control unit 32d, a recording unit 34d, a setting unit 38d, and a generating unit 39d, instead of the control unit 32c, the recording unit 34c, the setting unit 38c, and the generating unit 39 of the information processing apparatus 1c according to the third embodiment described above. Further, the information processing apparatus 1d further includes an image processor 40.

The control unit 32d is configured by using a CPU, an FPGA, a GPU, and the like, and controls the endoscope 400, the wearable device 500, and the display unit 20. The control unit 32d includes an operation history detection unit 326, in addition to the gaze detection controller 321, the speech input controller 322, the display controller 323, and the imaging controller 324.

The operation history detection unit 326 detects the contents of the operation of which the input is received by the operating unit 402 of the endoscope 400, and outputs a detection result thereof to the recording unit 34d. Specifically, in a case where an expand switch is operated from the operating unit 402 of the endoscope 400, the operation history detection unit 326 detects the operation contents, and outputs the detection result to the recording unit 34d. Furthermore, the operation history detection unit 326 may detect operation contents of a treatment tool that is inserted into the subject U4 through the endoscope 400, and may output the detection result to the recording unit 34d.

The recording unit 34d is configured by using a volatile memory, a non-volatile memory, a recording medium, and the like. The recording unit 34d further includes an operation history recording unit 346 in addition to the configuration of the recording unit 34c according to the third embodiment described above.

The operation history recording unit 346 records the history of the operation with respect to the operating unit 402 of the endoscope 400 that is input from the operation history detection unit 326.

The setting unit 38d assigns the important degree and the character information that is converted by the converter 35 to the speech data that is associated with a time axis identical to that of the gaze data, on the basis of the attention degree that is analyzed by the analysis unit 11 at each predetermined time interval and operation history that is recorded in the operation history recording unit 346 to be recorded in the recording unit 34d. Specifically, the setting unit 38d assigns the important degree (for example, a numerical value) for each frame of the speech data, on the basis of the attention degree that is analyzed by the analysis unit 11 and the operation history that is recorded in the operation history recording unit 346 to be recorded in the recording unit 34d. That is, the setting unit 38d performs processing of increasing the important degree as a coefficient that is set according to the contents of the operation history increases. The setting unit 38d is configured by using a CPU, an FPGA, a GPU, and the like.

The generating unit 39d generates gaze mapping data in which the attention degree that is analyzed by the analysis unit 11 and the character information are associated with an integrated image corresponding to integrated image data that is generated by the image processor 40, and outputs the generated gaze mapping data to the recording unit 34d and the display controller 323.

The image processor 40 generates the integrated image data of a three dimensional image by synthesizing a plurality of image data that are recorded in the image data recording unit 345, and outputs the integrated image data to the generating unit 39*d*.

Processing of Endoscope System

Figure 20:
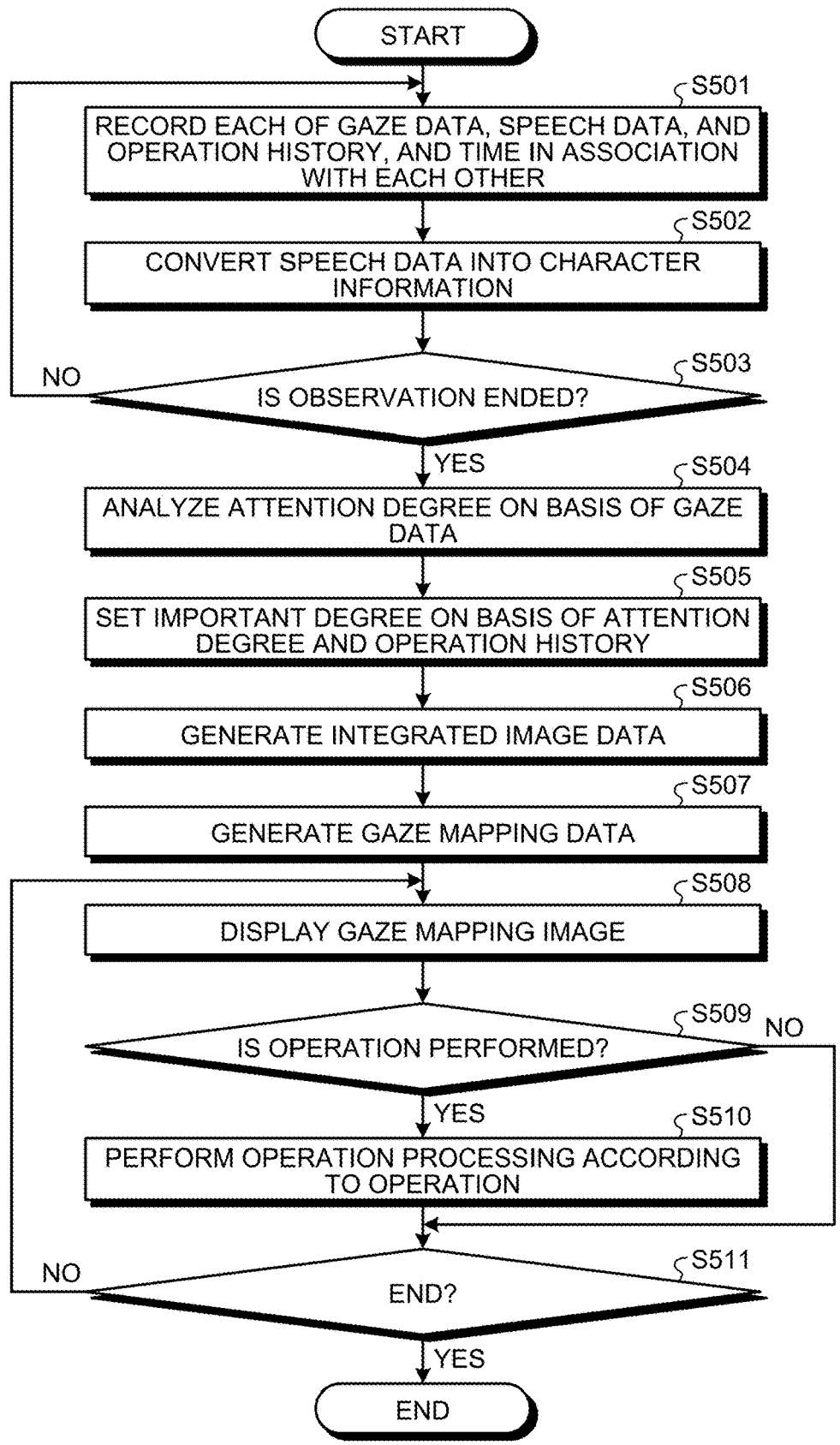
FIG. 20 is a flowchart illustrating an outline of processing that is executed by the endoscope system according to the fourth embodiment.

Next, processing that is executed by the endoscope system 300 will be described. FIG. 20 is a flowchart illustrating the output of the processing that is executed by the endoscope system 300.

As illustrated in FIG. 20, first, the control unit 32*d* associates each of the gaze data that is generated by the gaze detection unit 510, the speech data that is generated by the speech input unit 520, and the operation history that is detected by the operation history detection unit 326 with the time that is measured by the time measurement unit 33 to be recorded in the gaze data recording unit 341, the speech data recording unit 342, and the operation history recording unit 346 (Step S501).

After Step S501, the endoscope system 300 proceeds to Step S502 described below.

Step S502 to Step S504 respectively correspond to Step S303 to Step S305 of FIG. 12 described above. After Step S504, the endoscope system 300 proceeds to Step S505.

In Step S505, the setting unit 38*d* assigns the important degree and the character information that is converted by the converter 35 to the speech data that is associated with a time axis identical to that of the gaze data, on the basis of the attention degree that is analyzed by the analysis unit 11 at each predetermined time interval and the operation history that is recorded in the operation history recording unit 346 to be recorded in the recording unit 34*d*.

Figure 21:
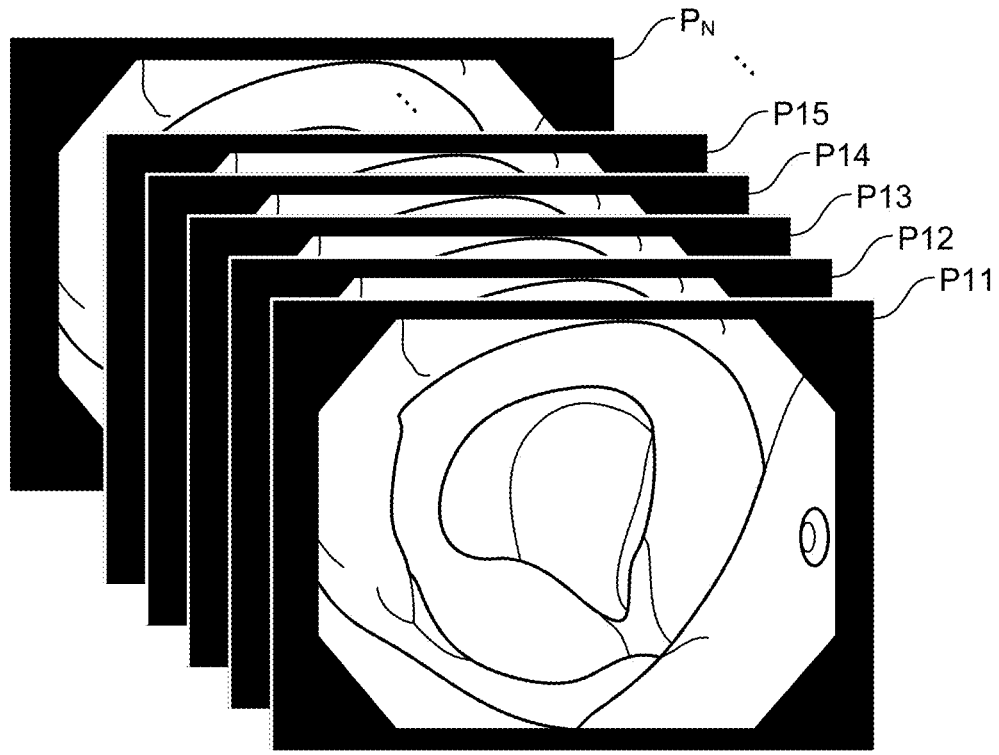
FIG. 21 is a diagram schematically illustrating an example of a plurality of images corresponding to a plurality of image data that are recorded in an image data recording unit according to the fourth embodiment.
Figure 22:
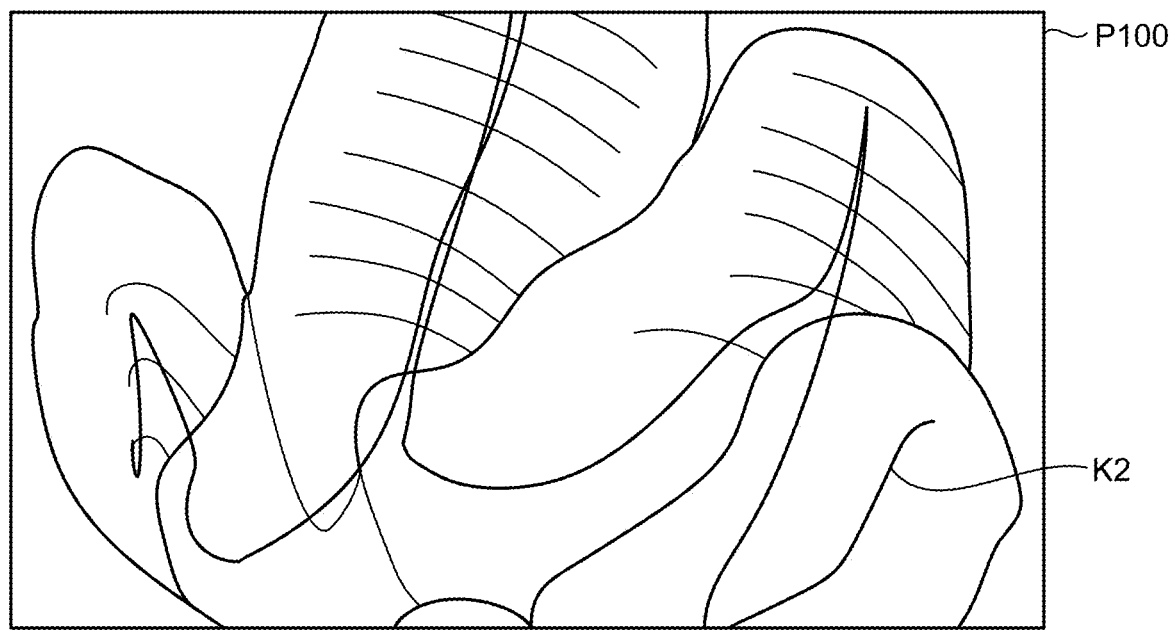
FIG. 22 is a diagram illustrating an example of an integrated image corresponding to integrated image data that is generated by an image processor according to the fourth embodiment.

Subsequently, the image processor 40 generates the integrated image data of the three dimensional image by synthesizing the plurality of image data that are recorded in the image data recording unit 345, and outputs the integrated image data to the generating unit 39*d* (Step S506). FIG. 21 is a diagram schematically illustrating an example of a plurality of images corresponding to the plurality of image data that are recorded in the image data recording unit 345. FIG. 22 is a diagram illustrating an example of an integrated image corresponding to the integrated image data that is generated by the image processor 40. As illustrated in FIG. 21 and FIG. 22, the image processor 40 generates an integrated image P100 corresponding to the integrated image data by synthesizing a plurality of temporally continuous image data P11 to P$_N$ (N=Integer).

After that, the generating unit 39*d* generates the gaze mapping data in which the attention degree that is analyzed by the analysis unit 11, the gaze and the character information are associated with the integrated image P100 corresponding to the integrated image data that is generated by the image processor 40, and outputs the generated gaze mapping data to the recording unit 34*d* and the display controller 323 (Step S507). In this case, the generating unit 39*d* may associate the operation history with the integrated image P100 corresponding to the integrated image data that is generated by the image processor 40, in addition to the attention degree that is analyzed by the analysis unit 11, a gaze K2, and the character information. After Step S507, the endoscope system 300 proceeds to Step S508 described below.

Step S508 to Step S511 respectively correspond to Step S308 to Step S311 of FIG. 12 described above.

According to the fourth embodiment described above, the setting unit 38*d* assigns the important degree and the character information that is converted by the converter 35 to the speech data associated with a time axis identical to that of the gaze data, on the basis of the attention degree that is analyzed by the analysis unit 11 and the operation history that is recorded in the operation history recording unit 346 to be recorded in the recording unit 34*d*, and thus, assigns the operation history and the important degree based on the attention degree to the speech data, and therefore, it is possible to understand an important period of the speech data to which the operation contents and the attention degree are added.

In addition, in the fourth embodiment, the endoscope system is described, but for example, a capsule type endoscope, a video microscope capturing a subject, a mobile phone having a capturing function, and a tablet type terminal having a capturing function can also be applied.

In addition, in the fourth embodiment, the endoscope system including a flexible endoscope is described, but an endoscope system including a rigid endoscope, and an endoscope system including an industrial endoscope can also be applied.

In addition, in the fourth embodiment, the endoscope system including the endoscope that is inserted into the subject is described, but a sinus endoscope, and an endoscope such as an electrosurgical knife or an inspection probe can also be applied.

Fifth Embodiment

Next, a fifth embodiment of the present disclosure will be described. In the first embodiment to the fourth embodiment described above, a case where there is one user is assumed, but in the fifth embodiment, a case where there are two or more users is assumed. Further, in the fifth embodiment, the information processing apparatus is incorporated in an information processing system in which an image is browsed by a plurality of users. Hereinafter, the configuration of a browsing system according to the fifth embodiment will be described, and then, processing that is executed by the information processing system according to the fifth embodiment will be described.

Furthermore, the same reference numerals will be applied to the same configurations as those of the information processing apparatus 1*b* according to the second embodiment described above, and the detailed description will be suitably omitted.

Configuration of Information Processing System

Figure 23:
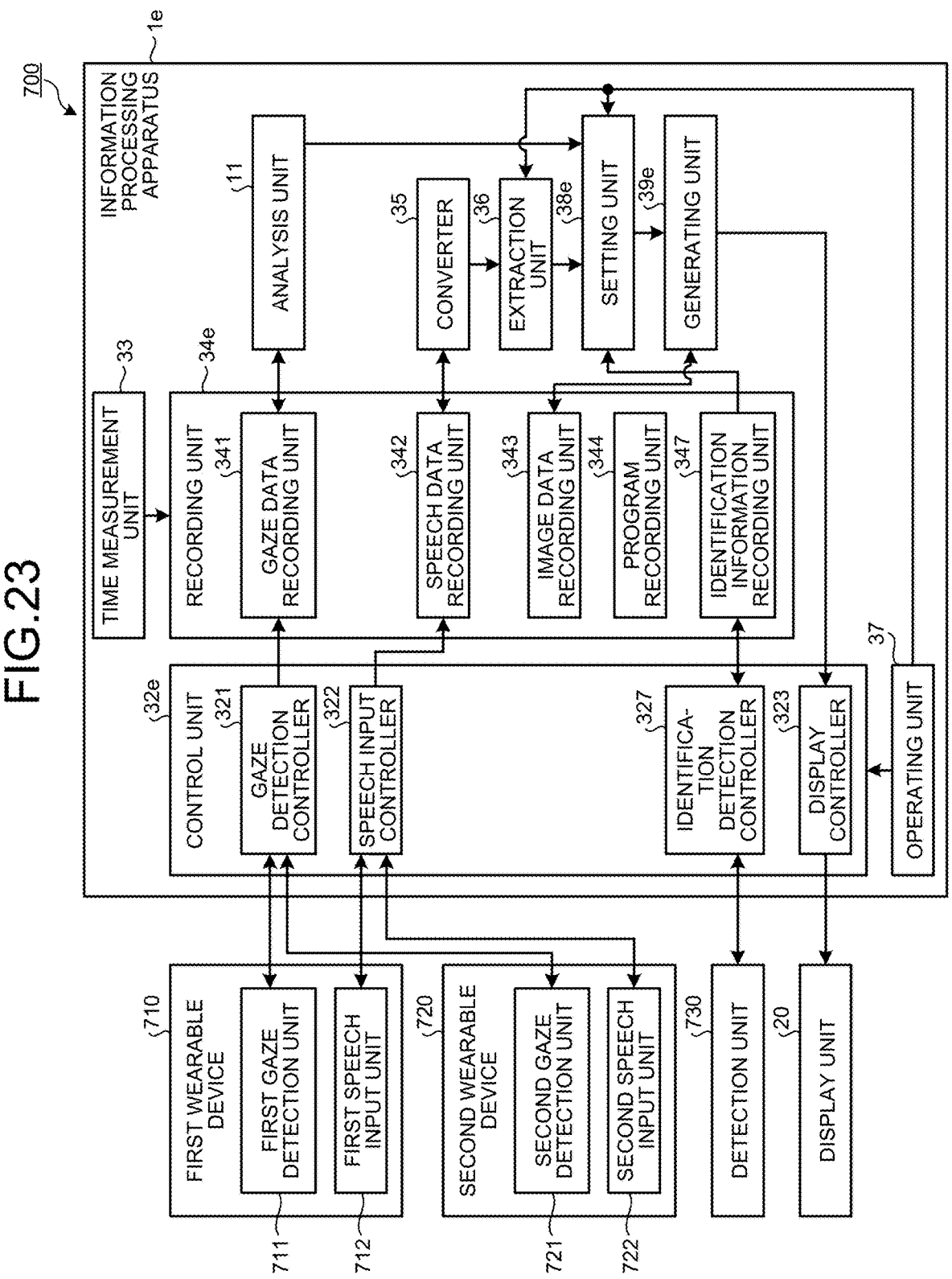
FIG. 23 is a block diagram illustrating a functional configuration of an information processing system according to a fifth embodiment.

FIG. 23 is a block diagram illustrating a functional configuration of the information processing system according to the fifth embodiment.

An information processing system 700 illustrated in FIG. 23 includes the display unit 20, a first wearable device 710, a second wearable device 720, a detection unit 730, and an information processing apparatus 1*e*.

Configuration of First Wearable Device

First, the configuration of the first wearable device 710 will be described.

The first wearable device 710 is mounted on the user, detects the gaze of the user, and receives the input of the speech of the user. The first wearable device 710 includes a first gaze detection unit 711 and a first speech input unit 712. The first gaze detection unit 711 and the first speech input unit 712 have the same configuration as that of the gaze detection unit 510 and the speech input unit 520 according to the fourth embodiment described above, and thus, the detailed configuration will be omitted.

Configuration of Second Wearable Device

Next, the configuration of the second wearable device 720 will be described.

The second wearable device 720 has the same configuration as that of the first wearable device 710 described above, is mounted on the user, detects the gaze of the user, and receives the input of the speech of the user. The second wearable device 720 includes a second gaze detection unit 721 and a second speech input unit 722. The second gaze detection unit 721 and the second speech input unit 722 have the same configuration as that of the gaze detection unit 510 and the speech input unit 520 according to the fourth embodiment described above, and thus, the detailed configuration will be omitted.

Configuration of Detection Unit

Next, the configuration of the detection unit 730 will be described.

The detection unit 730 detects identification information of identifying each of the plurality of users, and outputs a detection result to the information processing apparatus 1e. The detection unit 730 detects the identification information of the user from an IC card in which the identification information (for example, an ID, a name, or the like) of identifying each of the plurality of users is recorded, and outputs the detection result to the information processing apparatus 1e. The detection unit 730, for example, is configured by using a card reader that reads the IC card. Furthermore, the detection unit 730 may identify the user by using a feature point of the face of the user that is set in advance and known pattern matching, with respect to the image corresponding to the image data generated by capturing the face of the plurality of users, and may output an identification result to the information processing apparatus 1e. It is obvious that the detection unit 730 may identify the user on the basis of a signal that is input according to the operation from the operating unit 37, and may output the identification result to the information processing apparatus 1e.

Configuration of Information Processing Apparatus

Next, the configuration of the information processing apparatus 1e will be described.

The information processing apparatus 1e includes a control unit 32e, a recording unit 34e, and a setting unit 38e, instead of the control unit 32d, the recording unit 34d, and the setting unit 38d of the information processing apparatus 1d according to the fourth embodiment described above.

The control unit 32e is configured by using a CPU, an FPGA, a GPU, and the like, and controls the first wearable device 710, the second wearable device 720, the detection unit 730, and the display unit 20. The control unit 32e includes an identification detection controller 327, in addition to the gaze detection controller 321, the speech input controller 322, and the display controller 323.

The identification detection controller 327 controls the detection unit 730, identifies each of the plurality of users on the basis of an acquisition result acquired by the detection unit 730, and outputs the identification result to the recording unit 34e.

The recording unit 34e is configured by using a volatile memory, a non-volatile memory, a recording medium, and the like. The recording unit 34e further includes an identification information recording unit 347 in addition to the configuration of the recording unit 34 according to the second embodiment described above.

The identification information recording unit 347 records the identification information of each of the plurality of users that is input from the identification detection controller 327.

The setting unit 38e assigns the important degree and the character information that is converted by the converter 35 to the speech data associated with a time axis identical to that of the gaze data at each predetermined time interval, on the basis of an analysis result that is analyzed by the analysis unit 11, the character information that is extracted by the extraction unit 36, and the identification information that is recorded in the identification information recording unit 347 to be recorded in the recording unit 34e. Further, the setting unit 38e performs weighting of the important degree according to the identification information of each of the users that is recorded in the identification information recording unit 347. That is, the setting unit 38e performs processing of increasing the important degree as the user is important (for example, a rank set according to an official position).

Processing of Information Processing System

Next, processing that is executed by the information processing system 700 will be described. FIG. 24 is a flowchart illustrating the outline of the processing that is executed by the information processing system 700.

As illustrated in FIG. 24, the display controller 323 allows the display unit 20 to display the image corresponding to the image data that is recorded in the image data recording unit 343 (Step S601).

Subsequently, the control unit 32e associates each of the gaze data and the speech data that is generated by each of the first wearable device 710 and the second wearable device 720, and the identification information that is acquired by the detection unit 730 with the time that is measured by the time measurement unit 33 to be recorded in the gaze data recording unit 341, the speech data recording unit 342, and the identification information recording unit 347 (Step S602). After Step S602, the information processing system 700 proceeds to Step S603.

Step S603 and Step S604 respectively correspond to Step S303 and Step S304 of FIG. 12 described above. After Step S604, the information processing system 700 proceeds to Step S605 described below.

In Step S605, the analysis unit 11 analyzes the attention degree of the gaze of each of the users, on the basis of first gaze data that is generated by the first wearable device 710 and second gaze data that is generated by the second wearable device 720.

Subsequently, the setting unit 38e assigns the important degree and the character information that is converted by the converter 35 to each of the first speech data and the second speech data associated with a time axis identical to that of the gaze data, on the basis of each attention degree that is analyzed by the analysis unit 11 at each predetermined time interval, and the identification information that is recorded in the identification information recording unit 347 to be recorded in the recording unit 34e (Step S606).

Step S607 to Step S611 respectively correspond to Step S307 to Step S311 of FIG. 12 described above.

According to the fifth embodiment described above, the setting unit 38e assigns the important degree and the character information that is converted by the converter 35 to each of the first speech data and the second speech data associated with a time axis identical to that of the gaze data, on the basis of the attention degree of each of the users that is analyzed by the analysis unit 11, and the identification information that is recorded in the identification information recording unit 347 to be recorded in the recording unit 34e, and thus, the identification information and the important degree based on the attention degree are assigned to the first speech data or the second speech data, and thus, it is possible to understand an important period of the speech data to which the attention degree according to the user is added.

Furthermore, in the fifth embodiment, the setting unit 38e assigns the important degree and the character information that is converted by the converter 35 to each of the first speech data and the second speech data associated with a time axis identical to that of the gaze data to be recorded in the recording unit 34e, on the basis of the attention degree of each of the users analyzed by the analysis unit 11 and the identification information of each of the users that is recorded in the identification information recording unit 347, but is not limited thereto, and for example, may detect the position of each of the plurality of users, and may assign the important degree and the character information that is converted by the converter 35 to each of the first speech data and the second speech data, on the basis of a detection result and the attention degree of each of the users to be recorded in the recording unit 34e.

Other Embodiments

A plurality of constituents disclosed in the first embodiment to the fifth embodiment described above are suitably combined, and thus, various information processing apparatuses or information processing systems can be formed. For example, some constituents of all of the constituents described in the first embodiment to the fifth embodiment described above may be deleted. Further, the constituents described in the first embodiment to the fifth embodiment described above may be suitably combined.

In addition, in the first embodiment to the fifth embodiment, the "unit" that has been described above can be read as a "section", a "circuit", or the like. For example, the control unit can be read as a control section or a control circuit.

In addition, a program that is executed in the information processing apparatus according to the first embodiment to the fifth embodiment is file data in an installable format or an executable format, and is provided by being recorded in a recording medium that can be read by a computer, such as a CD-ROM, a flexible disk (FD), a CD-R, a digital versatile disk (DVD), a USB medium, and a flash memory.

In addition, the program that is executed in the information processing apparatus according to the first embodiment to the fifth embodiment may be stored on a computer that is connected to a network such as the internet, and may be provided by being downloaded through the network. Further, the program that is executed in the information processing apparatus according to the first embodiment to the fifth embodiment may be provided or distributed through a network such as the internet.

In addition, in the first embodiment to the fifth embodiment, the signal is transmitted from various devices through a transmission cable, but for example, it is not necessary to transmit the signal in a wired manner, and the signal may be transmitted wirelessly. In this case, it is sufficient that the signal is transmitted from each of the devices, according to a predetermined wireless communication standard (for example, Wi-Fi (Registered Trademark) or Bluetooth (Registered Trademark)). It is obvious that wireless communication may be performed according to other wireless communication standards.

Furthermore, herein, in the description of the flowchart, an anteroposterior relationship of the pieces of processing between steps is explicitly described by using the expression of "first", "after that", "subsequently", and the like, but the order of processing that is necessary for carrying out the present disclosure is not uniquely determined by the expression. That is, the order of the processing in the flowchart described herein can be changed without contradiction.

According to the present disclosure, an effect is obtained in which an important period of the speech data that is simultaneously recorded can be understood on the basis of a dynamic state of the gaze.

As described above, some embodiments of the present invention have been described in detail on the basis of the drawings, but the embodiments are merely an example, and it is possible to carry out the present invention not only in the aspects described at the beginning of the present invention but also in other forms in which various modifications and improvements are made on the basis of the knowledge of a person skilled in the art.

What is claimed is:
1. An information processing apparatus comprising:
 a processor comprising hardware, the processor being configured to:
  analyze an attention degree of a gaze of a user, on the basis of gaze data in which the gaze of the user is detected, the gaze data being input externally,
  convert a speech data of the user into character information, the speech data being input externally, the speech data being associated with a time axis that is a same as that of the gaze data to be recorded in a memory,
  generate gaze mapping data in which the analyzed attention degree and coordinate information of the attention degree are associated with an image corresponding to an image data that is input externally, and
  display a gaze mapping image corresponding to the gaze mapping data on a display.
2. The information processing apparatus according to claim 1, wherein the processor is further configured to:
 extract the converted character information associated with an operation signal that is input externally, and
 extract the gaze data associated with the speech data of the extracted character information, and display the extracted gaze data with emphasis thereon.
3. An information processing apparatus further comprising:
 a processor comprising hardware, the processor being configured to:
  analyze an attention degree of a gaze of a user, on the basis of gaze data in which the gaze of the user is detected, the gaze data being input from a gaze detector that generates the gaze data by continuously detecting the gaze of the user, and
  assign an important degree according to the attention degree that is analyzed with respect to speech data of the user, the speech data being input from a speech input device that generates the speech data by receiving input of a speech of the user, the speech data being associated with a time axis that is a same as that of the gaze data to be recorded in a memory,
 wherein the gaze detector is provided in an eyepiece of a microscope, the user observes an observation image of the specimen through the eyepiece, the microscope having a variable observation magnification for observing the specimen, an imaging sensor is connected to the microscope, the imaging sensor generating image data by capturing the observation image of the specimen that is formed by the microscope, and the processor is further configured to perform weighting of the important degree according to the observation magnification.

4. An information processing apparatus comprising:

a processor comprising hardware, the processor being configured to, analyze an attention degree of a gaze of a user, on the basis of gaze data in which the gaze of the user is detected, the gaze data being input externally, assign an important degree according to the attention degree that is analyzed with respect to speech data of the user, the speech data being input externally, the speech data being associated with a time axis that is a same as that of the gaze data to be recorded in a memory, receive image data from an imaging sensor provided in an endoscope, the imaging sensor being provided on a tip end portion of an insertion portion insertable into a subject, the imaging sensor generating the image data by capturing an in-vivo image of the subject, and receive and record various operations for changing a field of view from an operating unit that is provided in the endoscope and receive input of the various operations.

5. The information processing apparatus according to claim 4, wherein the processor performs the weighting of the important degree on the basis of operation history relevant to operation history that is received by the operating unit.

* * * * *